US011091806B2

(12) United States Patent
Opiteck et al.

(10) Patent No.: US 11,091,806 B2
(45) Date of Patent: Aug. 17, 2021

(54) GENETIC MARKERS ASSOCIATED WITH RESPONSE TO CRTH2 RECEPTOR ANTAGONISTS

(71) Applicant: Merck Sharp & Dohme Corp., Rahway, NJ (US)

(72) Inventors: Gregory J. Opiteck, Milltown, NJ (US); Peggy H. Wong, Summit, NJ (US); Joshua McElwee, Jamaica Plains, MA (US); Devan V. Mehrotra, Lansdale, PA (US); Steven Greenberg, East Hanover, NJ (US); Zifang Guo, Audubon, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 253 days.

(21) Appl. No.: 15/745,926

(22) PCT Filed: Jul. 21, 2016

(86) PCT No.: PCT/US2016/043234
§ 371 (c)(1),
(2) Date: Jan. 18, 2018

(87) PCT Pub. No.: WO2017/015418
PCT Pub. Date: Jan. 26, 2017

(65) Prior Publication Data
US 2018/0237856 A1    Aug. 23, 2018

Related U.S. Application Data

(60) Provisional application No. 62/196,128, filed on Jul. 23, 2015.

(51) Int. Cl.
| *C12Q 1/68* | (2018.01) |
| *C12Q 1/6883* | (2018.01) |
| *A61K 31/437* | (2006.01) |
| *A61K 31/47* | (2006.01) |
| *C07D 215/14* | (2006.01) |
| *C07D 471/04* | (2006.01) |
| *A61K 45/06* | (2006.01) |

(52) U.S. Cl.
CPC .......... *C12Q 1/6883* (2013.01); *A61K 31/437* (2013.01); *A61K 31/47* (2013.01); *A61K 45/06* (2013.01); *C07D 215/14* (2013.01); *C07D 471/04* (2013.01); *C12Q 2600/106* (2013.01); *C12Q 2600/156* (2013.01)

(58) Field of Classification Search
None
See application file for complete search history.

(56) References Cited

U.S. PATENT DOCUMENTS

| 7,666,878 B2 | 2/2010 | Bala et al. |
| 8,394,819 B2* | 3/2013 | Berthelette .......... C07D 471/04 514/294 |
| 8,592,383 B2 | 11/2013 | Huang et al. |
| 2005/0119268 A1 | 6/2005 | Middlemiss |
| 2011/0200583 A1 | 8/2011 | Hakonarson et al. |

FOREIGN PATENT DOCUMENTS

| CN | 104726601 | 6/2015 |
| CN | 104726601 A | 6/2015 |
| EP | 2508602 A1 | 10/2012 |
| EP | 2548876 A1 | 1/2013 |
| RU | 2412934 C2 | 2/2011 |
| WO | 2005044260 A1 | 5/2005 |
| WO | 2014100312 A1 | 6/2014 |

OTHER PUBLICATIONS

EP Search Report—16828511.1—dated Mar. 29, 2019.
Wang, Y-H et al, UGT2B17 Genetic Polymorphisms Dramatically Affect the Pharmacokinetics of MK-7246 in Healthy Subjects in a First-in-Human Study, Clinical Pharmacology and Therapeutics, 2012, 96-102, vol. 92, No. 1.
Xue, L et al, Prostaglandin D2 and leukotriene E4 synergize to stimulate diverse TH2 functions and TH2 cell/neutrophil crosstalk, Journal of ALlergy and Clinical Innumology, 2014, 1358-1366, vol. 135, No. 5.
Charles et al., New Evidence and Novel Therapies for Severe Asthma Management, EMJ Respir., 2014, 50-57, 2.
Huang et al., Sequence Variants of the Gene Encodign Chemoattractant Receptor Expressed on Th2 Cells (CRTH2) are Associated with Asthma and Differentially Influence mRNA Stability, Human Molecular Genetics, 2004, pp. 2691-2697, 13:21.
International Search Report and Written Opinion for PCT/US2014/043234, dated Oct. 24, 2016, 12 pages.
Ishizuka et al., Ramatroban (BAY u3405): A Novel Dual Antagonist of TXA2, Receptor and CRTh2, a Newly Identified Prostaglandin D2 Receptor, Cardiovascular Drug Review, 2004, 50-57, 22.
Kersey et al., Ensembl Genomes 2013: Scaling up Access to Genome-Wide, Nucleic Acids Research, 2014, D546-D552, 42.
Lukacs et al., CRTH2 Antagonism Significantly Ameliorates Airway Hyperreactivity and Downregulates Inflammation-Induced Genes in a Mouse Model of Airway Inflammation, Am J. Physiol Lung Cell Mol. Physiol, 2008, pp. 767-779, 295.
Okada, et al., Idenfitifcation of Nine Novel Loci Associated with White Blood Cell Subtypes in a Japanese Population, PLoS Genetics, 2011, 1-10, vol. 7, Issue 6.

(Continued)

*Primary Examiner* — Jehanne S Sitton
(74) *Attorney, Agent, or Firm* — Eric A. Meade; John C. Todaro

(57) ABSTRACT

The present invention provides genetic markers on human chromosome 1 that are associated with a beneficial response to CRTH2 receptor antagonists. These CRTH2 receptor antagonist response markers are useful, inter alia, to identify patients who are most likely to benefit from treatment with CRTH2 receptor antagonist compositions and drug products, in methods of treating patients having a disease susceptible to treatment with a CRTH2 receptor antagonist, and in methods for selecting the most appropriate therapy for such patients.

5 Claims, 4 Drawing Sheets

Specification includes a Sequence Listing.

(56) References Cited

OTHER PUBLICATIONS

Shichijo et al., A Prostaglandin D2 Receptor Antagonist Modifies Experimental Asthma in Sheep, Experimental Models of Allergic Disease, 2009, pp. 1404-1414, 39.
SINGULAIR—Highlights of Prescribing Information, Initial US Approval 1998; revised Jun. 2016.
Uller et al., Antagonism of the Prostaglandin D2 Receptor CRTH2 Attenuates Asthma Pathology in Mouse Eosinophilic Airway Inflammation, Respiratory Research, 2007, pp. 1-10, 8:16.

* cited by examiner rs12748961
CTCTTCACTATGTTGAAATTGGGTC[C/T]TTCTTCCCCAAAGATTGAAGAGAAT rs12118655
TCAGATGGGAAATATTGCAGGGGCT[A/G]TATGGTCTCCATCGCAACTACTCAC rs6679073
TTTTGAGACTGGCAAATGTTCTGCA[A/C]CCAGTATCTGCTCAATACTTTTGTG rs12564209
CAAAAGTCTTTAGGATAGTCTCTGG[C/G]TCACAGTAAGTGCTACGTAAGTGTT rs3805
TTTTTATACATGTTATTTTAGGGCA[A/G/T]AAGCTGAGTACTATACCCCCACACC rs71633561
GAGGTAGGAGAATCACTTGAACCCA[C/G]GGGTCAGAGGTTGTGGTGAGCCGAG rs71970505
AGTTTGCAAAGTAACCCATTTGGCC[-/ATGCAGACTGT]AAGTCATACAACTCTAGAGGGACAA rs12132270
CTCCTATCTCCATTTTACTCTTATG[C/T]CTACCCCCAGAATAGGTTTTCTGGA rs67625805
GGTGGTAATGTATATTTATCTTAAA[-/T]TTTTTTTTTTTTTTTGAGACGGAGT rs3747992
GCGGATCGCCTGAGATCAGGAGTTC[A/G]AGACCAGCCTGGCCAACATGGTGAA rs11557080
CGCAATGGTGTGATCTCAGCTCACT[A/G]CAACCTCTAACTCCCAGGTTCAAGC rs71633563
CTGCCTACAAAAGTATCAGGCAAGA[C/T]AGGCCTCACGTTAGATGAGATAGTA rs34848415
GGCAATAAGAGTGAAACTCCATCTC[-/A]AAAAAAAAAAAAAAAAAATCTATTT rs1891091
ACCTCCTCCCATAAATTGCAGAATC[A/G]ATTCCCTTCCTGCCCACTCTCAGTG

FIG. 1

GENETIC MARKERS ASSOCIATED WITH RESPONSE TO CRTH2 RECEPTOR ANTAGONISTS

CROSS REFERENCE TO RELATED APPLICATIONS

This application is a U.S. National Phase application under 35 U.S.C. § 371 of PCT Application No. PCT/US2016/043234, filed Jul. 21, 2016, which claims priority under 35 U.S.C. § 119(e) from provisional Application No. 62/196,128, filed Jul. 23, 2015.

FIELD OF THE INVENTION

The present invention relates to genetic markers on human chromosome 1 that are predictive of a beneficial response to therapy with CRTH2 receptor antagonists.

BACKGROUND OF THE INVENTION

Identification of any publication in this section or any section of this application is not an admission that such publication is prior art to the present invention.

Asthma is a highly prevalent disease associated with significant morbidity and mortality, and accounting for high direct and indirect healthcare expenditures. World Health Organization (WHO) data currently estimate the prevalence of asthma to be 300 million individuals worldwide, with this number expected to increase to 400 million by 2025. It is estimated that approximately 15 million disability adjusted life years are lost to asthma, and one in 250 deaths is due to asthma. Masoli M, et al., for the Global Initiative for Asthma (GINA) Program, *Allergy* 2004; 59:469-78. This high disease burden is in part due to patients who are not well controlled on standard therapy. Bateman E D, et al., *Am J Respir Crit Care Med* 2004; 170:836-44. In addition, compliance with standard inhaler therapy is relatively low. It is estimated that 44.2% and 51.5% of patients who begin a combination and concurrent inhalational therapy, respectively, do not renew their initial prescription during the first year. Marceau C, et al., *J. Allergy Clin Immunol* 2006; 118:574-81. Alternative options to inhalers include oral agents, such as montelukast and zileuton, as well as methylxanthines such as aminophylline; however, these agents are recognized to be less potent than inhaled agents. Therefore, a need exists for new, well-tolerated oral therapies that effectively treat asthma, either alone or in combination with available therapies.

Chemoattractant Receptor-homologous molecule on Th2 cells (CRTH2) is a G protein-coupled receptor for the prostaglandin D2 (PGD2) expressed on eosisnophils, basophils and Th2 cells. In vitro, PGD2 and some of its CRTH2-selective metabolites can recruit and activate these leukocytes by 1) stimulating the expression of the surface protein CD11b which favors cell adhesion to the vascular wall and transmigration of cells from the blood circulation to the inflamed tissue and 2) stimulating cell movement to the site of inflammation (chemotaxis). CRTH2 activation also leads to the stimulation of Th2 cytokines release, such as IL-13 from the TH2 cells and to the stimulation of basophil and eosinophil degranulation.

Existing pre-clinical and clinical data suggest that the PGD2/CRTH2 pathway is fundamental to the recruitment and activation of key pro-inflammatory leukocytes contributing to asthma. Shichijo M, Arimura A, Hirano Y, et al. *Clin Exp Allergy* 2009 September; 39(9):1404-14; Lukacs N W, Berlin A A, Franz-Bacon K, et al. *Am J Physiol Lunch Cell Mol Physiol* 2008:295:L767-79; Uller L, Mathiesen J M, Alenmyr L, et al. *Respir Res* 2007; 8:16I. In humans, a CRTH2 genetic polymorphism leading to increased CRTH2 mRNA stability is significantly associated with asthma in two independent populations. Huang J-L, Gao P-S, Mathias R A, Yao T-C, Chen L-C, Kuo M-L, et al. *Hum Mol Genet* 2004; 13(21):2691-7. Ramatroban, a dual TP/CRTH2 antagonist is reported to exhibit some degree of efficacy in allergic rhinitis and is commercialized in Japan. Ishizuka T, Matsui T, Okamoto Y, et al., *Cardiovasc Drug Rev* 2004; 22:71-90. Furthermore a recent Phase IIa clinical study conducted in a patient population afflicted with eosinophilic severe asthma, demonstrated reduction of sputum eosinophils in patients treated with of the CRTH2 antagonist, fevipiprant. *European Medical Journal Respir.* 2014; 2:50-57. Taken together, these findings are consistent with a potentially important role for CRTH2 inhibition in the treatment of asthma.

The therapeutic effect of CRTH2 receptor antagonists can vary widely among patients afflicted with asthma. In order to better target patients who might respond better to CRTH2 receptor and thereby provide a better and more cost-effective treatments for asthma, a need exists for a way of identifying patients who are most likely to benefit through treatments with CRTH2 receptor antagonists. This invention addresses that need.

SUMMARY OF THE INVENTION

The present invention is based on the discovery that genetic polymorphisms such as single nucleotide polymorphisms (SNP) on human chromosome 1 are significantly associated with response to treatment with CRTH2 receptor antagonists in patients suffering from a disorder associated with CRTH2 receptor function. The genetic polymorphisms associated with response to CRTH2 receptor antagonist therapy are referred to herein as the "CRTH2 antagonist response markers."

One of these genetic polymorphisms is a SNP which is a C/T polymorphism, identified as rs12748961 in the NCBI SNP Database. The presence of the C allele is associated with a better treatment response, with the C/C or C/T genotype associated with a 4.5-fold better improvement in Forced Expiratory Volume in one second ($FEV_1$) in asthmatic patients. While the C allele is the minor allele in Caucasians, since it is present at a substantially higher frequency in a population of Asian ancestry than in the overall population, the rs12748961 polymorphism may guide medical practitioners, health authorities, and medical insurance providers in selecting a suitable population of asthmatic patients which might benefit from CRTH2 receptor antagonist therapy.

The inventors also identified associations between other genetic polymorphisms on chromosome 1 with a beneficial response to a CRTH2 receptor antagonist, e.g., improvements in $FEV_1$ score in asthmatic patients. The genetic polymorphisms associated with a beneficial response to CRTH2 receptor antagonist therapy are described in Table 1 below, wherein PS means polymorphic site according to the SNP NCBI database and "-" in the second column indicates that the variant represents a deletion or insertion variant.

TABLE 1

CRTH2 Antagonist Response Markers

| Polymorphic Site (PS) | Alleles | Better Response Allele |
|---|---|---|
| rs12748961 | T/C | C |
| rs12118655 | A/G | G |
| rs6679073 | C/A | A |
| rs12564209 | C/G | G |
| rs3805 | T/G/A | G |
| rs71633561 | G/C | C |
| rs71970505 | ATGCAGACTGT/- | - |
| rs12132270 | C/T | T |
| rs67625805 | T/- | - |
| rs3747972 | A/G* | A |
| rs11557080 | G/A | A |
| rs71633563 | C/T | T |
| rs34848415 | A/- | - |
| rs1891091 | A/G* | A |

*The NCBI database indicates that rs3747972 and rs1891091 are RefSNP Alleles for the reverse strands.

In Table 1, the designations of "-" as entries in columns 2, indicate that the variant is a deletion or insertion variant. For instance, in rs67625805, the alternate allele represents a deletion of the T nucleotide at the corresponding position. As another example, in rs71970505, a 11-residue nucleotide segment is absent in one of the alleles, where as in the alternative allele, the nucleotide segment ATGCAGACTGT is present at the corresponding position of the nucleotide sequence.

The inventors herein contemplate that testing individuals for the presence of at least one or more of the CRTH2 Antagonist Response Markers in Table 1 will be useful in a variety of pharmacogenetic products and methods that involve identifying subjects most likely to respond to therapy for CRTH2 receptor antagonists for disorders susceptible to treatment with CRTH2 receptor antagonists, and in helping physicians decide whether to prescribe a CRTH2 receptor antagonist to a patient afflicted with asthma. For instance, the inventors contemplate that testing subjects for the presence of at least one copy of the C allele for the rs12748961 SNP will be useful for such products and methods, and in helping such physicians.

Accordingly, in embodiment no. 1, the invention provides method of treating a patient with a disorder susceptible to treatment with a CRTH2 receptor antagonist comprising:

administering a therapeutically effective amount of the CRTH2 receptor antagonist to the patient, wherein said patient, prior to the administration of the CRTH2 receptor antagonist, has tested positive for at least one copy of a better response allele selected from a CRTH2 receptor antagonist marker selected from Table 1 above.

In a first aspect of embodiment no. 1, said patient, prior to the administration of the CRTH2 receptor antagonist, has tested positive for at least one copy of the C allele of the rs12748961 SNP.

In a second aspect of embodiment no. 1, said patient, prior to the administration of the CRTH2 receptor antagonist, has tested positive for at least one copy of the G allele of the rs12118655 SNP.

In a third aspect of embodiment no. 1, said patient, prior to the administration of the CRTH2 receptor antagonist, has tested positive for at least one copy of the A allele of the rs6679073 SNP.

In a fourth aspect of embodiment no. 1, said patient, prior to the administration of the CRTH2 receptor antagonist, has tested positive for at least one copy of the G allele of the rs12564209 SNP.

In a fifth aspect of embodiment no. 1, said patient, prior to the administration of the CRTH2 receptor antagonist, has tested positive for at least one copy of the G allele of the rs3805 SNP.

In a sixth aspect of embodiment no. 1, said patient, prior to the administration of the CRTH2 receptor antagonist, has tested positive for at least one copy of the C allele of the rs71633561 SNP.

In a seventh aspect of embodiment no. 1, said patient, prior to the administration of the CRTH2 receptor antagonist, has tested positive for at least one copy of the deletion allele of the rs71970505 SNP (indicated as "-" in the Better Response Allele column of Table 1).

In an eighth aspect of embodiment no. 1, said patient, prior to the administration of the CRTH2 receptor antagonist, has tested positive for at least one copy of the T allele of the rs12132270 SNP.

In a ninth aspect of embodiment no. 1, said patient, prior to the administration of the CRTH2 receptor antagonist, has tested positive for at least one copy of the deletion allele of the rs67625805 SNP (indicated as "-" in the Better Response Allele column of Table 1).

In a tenth aspect of embodiment no. 1, said patient, prior to the administration of the CRTH2 receptor antagonist, has tested positive for at least one copy of the A allele of the rs3747972 SNP.

In an eleventh aspect of embodiment no. 1, said patient, prior to the administration of the CRTH2 receptor antagonist, has tested positive for at least one copy of the A allele of the rs11557080 SNP.

In a twelfth aspect of embodiment no. 1, said patient, prior to the administration of the CRTH2 receptor antagonist, has tested positive for at least one copy of the T allele of the rs71633563 SNP.

In a thirteenth aspect of embodiment no. 1, said patient, prior to the administration of the CRTH2 receptor antagonist, has tested positive for at least one copy of the deletion allele of the rs34848415 SNP (indicated as "-" in the Better Response Allele column of Table 1).

In a fourteenth aspect of embodiment no. 1, said patient, prior to the administration of the CRTH2 receptor antagonist, has tested positive for at least one copy of the A allele of the rs1891091 SNP.

In a fifteenth aspect of embodiment no. 1 (including any one of the first-fourteenth aspects), the method further comprises administering a leukotriene antagonist such as montelukast, zafilukast, or pranlukast to the patient. In a sixteenth aspect of embodiment no. 1 (including any one of the first-fifteenth aspects), the method further comprises administering montelukast to the patient.

In embodiment no. 2, the invention provides a drug product which comprises a pharmaceutical composition and prescribing information, wherein the pharmaceutical composition comprises a CRTH2 receptor antagonist and the prescribing information comprises a pharmacogenetic indication, wherein the pharmacogenetic indication comprises the treatment of a disease susceptible to treatment with the CRTH2 receptor antagonist in patients who test positive for at least one copy of a better response allele selected from a CRTH2 receptor antagonist marker as set forth in Table 1 above.

In a first aspect of embodiment no. 2, the pharmacogenetic indication comprises the treatment of a disease susceptible to treatment with the CRTH2 receptor antagonist in patients who test positive for at least one copy of the C allele of the rs12748961 SNP.

In a second aspect of embodiment no. 2, the pharmacogenetic indication comprises the treatment of a disease susceptible to treatment with the CRTH2 receptor antagonist in patients who test positive for at least one copy of the G allele of the rs12118655 SNP.

In a third aspect of embodiment no. 2, the pharmacogenetic indication comprises the treatment of a disease susceptible to treatment with the CRTH2 receptor antagonist in patients who test positive for at least one copy of the A allele of the rs6679073 SNP.

In a fourth aspect of embodiment no. 2, the pharmacogenetic indication comprises the treatment of a disease susceptible to treatment with the CRTH2 receptor antagonist in patients who test positive for at least one copy of the G allele of the rs12564209 SNP.

In a fifth aspect of embodiment no. 2, the pharmacogenetic indication comprises the treatment of a disease susceptible to treatment with the CRTH2 receptor antagonist in patients who test positive for at least one copy of the G allele of the rs3805 SNP.

In a sixth aspect of embodiment no. 2, the pharmacogenetic indication comprises the treatment of a disease susceptible to treatment with the CRTH2 receptor antagonist in patients who test positive for at least one copy of the C allele of the rs71633561 SNP.

In a seventh aspect of embodiment no. 2, the pharmacogenetic indication comprises the treatment of a disease susceptible to treatment with the CRTH2 receptor antagonist in patients who test positive for at least one copy of the deletion allele of the rs71970505 SNP.

In an eighth aspect of embodiment no. 2, the pharmacogenetic indication comprises the treatment of a disease susceptible to treatment with the CRTH2 receptor antagonist in patients who test positive for at least one copy of the T allele of the rs12132270 SNP.

In a ninth aspect of embodiment no. 2, the pharmacogenetic indication comprises the treatment of a disease susceptible to treatment with the CRTH2 receptor antagonist in patients who test positive for at least one copy of the deletion allele of the rs67625805 SNP.

In a tenth aspect of embodiment no. 2, the pharmacogenetic indication comprises the treatment of a disease susceptible to treatment with the CRTH2 receptor antagonist in patients who test positive for at least one copy of the A allele of the rs3747972 SNP.

In an eleventh aspect of embodiment no. 2, the pharmacogenetic indication comprises the treatment of a disease susceptible to treatment with the CRTH2 receptor antagonist in patients who test positive for at least one copy of the A allele of the rs11557080 SNP.

In a twelfth aspect of embodiment no. 2, the pharmacogenetic indication comprises the treatment of a disease susceptible to treatment with the CRTH2 receptor antagonist in patients who test positive for at least one copy of the T allele of the rs71633563 SNP.

In a thirteenth aspect of embodiment no. 2, the pharmacogenetic indication comprises the treatment of a disease susceptible to treatment with the CRTH2 receptor antagonist in patients who test positive for at least one copy of the deletion allele of the rs34848415 SNP.

In a fourteenth aspect of embodiment no. 2, the pharmacogenetic indication comprises the treatment of a disease susceptible to treatment with the CRTH2 receptor antagonist in patients who test positive for at least one copy of the A allele of the rs1891091 SNP.

In a fifteenth aspect of the drug product set forth in embodiment no. 2 (including any one of the first-fourteenth aspects), the drug product further comprises a leukotriene antagonist such as montelukast, zafilukast, or pranlukast. In a sixteenth aspect of embodiment no. 2 (including any one of the first-fourteenth aspects) the drug product further comprises montelukast.

In embodiment no. 3, the invention provides the use of a CRTH2 receptor antagonist in the manufacture of a medicament for treating a patient having a disease susceptible to treatment with a CRTH2 receptor antagonist and a positive test for at least one copy of the better response allele selected from a CRTH2 receptor antagonist marker as set forth in Table 1 above.

In a first aspect of embodiment no. 3, the patient has a positive test for at least one copy of the C allele of the rs12748961 SNP.

In a second aspect of embodiment no. 3, the patient has a positive test for at least one copy of the G allele of the rs12118655 SNP.

In a third aspect of embodiment no. 3, the patient has a positive test for at least one copy of the A allele of the rs6679073 SNP.

In a fourth aspect of embodiment no. 3, the patient has a positive test for at least one copy of the G allele of the rs12564209 SNP.

In a fifth aspect of embodiment no. 3, the patient has a positive test for at least one copy of the G allele of the rs3805 SNP.

In a sixth aspect of embodiment no. 3, the patient has a positive test for at least one copy of the C allele of the rs71633561 SNP.

In a seventh aspect of embodiment no. 3, the patient has a positive test for at least one copy of the deletion allele of the rs71970505 SNP.

In an eighth aspect of embodiment no. 3, the patient has a positive test for at least one copy of the T allele of the rs12132270 SNP.

In a ninth aspect of embodiment no. 3, the patient has a positive test for at least one copy of the deletion allele of the rs67625805 SNP.

In a tenth aspect of embodiment no. 3, the patient has a positive test for at least one copy of the A allele of the rs3747972 SNP.

In an eleventh aspect of embodiment no. 3, the patient has a positive test for least one copy of the A allele of the rs11557080 SNP.

In a twelfth aspect of embodiment no. 3, the patient has a positive test for at least one copy of the T allele of the rs71633563 SNP.

In a thirteenth aspect of embodiment no. 3, the patient has a positive test for at least one copy of the deletion allele of the rs34848415 SNP.

In a fourteenth aspect of embodiment no. 3, the patient has a positive test for at least one copy of the A allele of the rs1891091 SNP.

In embodiment no. 4, the invention provides a method of selecting a therapy for treating a patient having a disease susceptible to treatment with a CRTH2 receptor antagonist, in which a patient's genotype at a polymorphic site selected from those set forth in Table 1 is determined and reported, the method comprising:

consulting the report to identify that the patient has at least one copy of the better response allele of the CRTH2 antagonist response marker; and based on that consultation, treating the patient with the CRTH2 receptor antagonist.

In a first aspect of embodiment no. 4, the report is consulted to identify that the patient has at least one copy of the C allele of the rs12748961 SNP.

In a second aspect of embodiment no. 4, the report is consulted to identify that the patient has at least one copy of the G allele of the rs12118655 SNP.

In a third aspect of embodiment no. 4, the report is consulted to identify that the patient has at least one copy of the A allele of the rs6679073 SNP.

In a fourth aspect of embodiment no. 4, the report is consulted to identify that the patient has at least one copy of the G allele of the rs12564209 SNP.

In a fifth aspect of embodiment no. 4, the report is consulted to identify that the patient has at least one copy of the G allele of the rs3805 SNP.

In a sixth aspect of embodiment no. 4, the report is consulted to identify that the patient has at least one copy of the C allele of the rs71633561 SNP.

In a seventh aspect of embodiment no. 4, the report is consulted to identify that the patient has at least one copy of the deletion allele of the rs71970505 SNP.

In an eighth aspect of embodiment no. 4, the report is consulted to identify that the patient has at least one copy of the T allele of the rs12132270 SNP.

In a ninth aspect of embodiment no. 4, the report is consulted to identify that the patient has at least one copy of the deletion allele of the rs67625805 SNP.

In a tenth aspect of embodiment no. 4, the report is consulted to identify that the patient has at least one copy of the A allele of the rs3747972 SNP.

In an eleventh aspect of embodiment no. 4, the report is consulted to identify that the patient has at least one copy of the A allele of the rs11557080 SNP.

In a twelfth aspect of embodiment no. 4, the report is consulted to identify that the patient has at least one copy of the T allele of the rs71633563 SNP.

In a thirteenth aspect of embodiment no. 4, the report is consulted to identify that the patient has at least one copy of the deletion allele of the rs34848415 SNP.

In a fourteenth aspect of embodiment no. 4, the report is consulted to identify that the patient has at least one of the A allele of the rs1891091 SNP.

In embodiment no. 5, the invention provides a screening method for selecting patients for treatment with a CRTH2 receptor antagonist from a group of patients having a disorder susceptible to treatment with the CRTH2 receptor antagonist, comprising testing each member of the group for the presence of at least one copy of the better response allele of a CRTH2 antagonist response marker selected from those set forth in Table 1 above, wherein a positive test is the presence of at least one copy of the better response allele of the CRTH2 antagonist response marker.

In a first aspect of embodiment no. 5, each member of the group is tested for the presence of at least one copy of the C allele of the rs12748961 SNP, wherein a positive test is the presence of at least one copy of the C allele of the rs12748961 SNP.

In a second aspect of embodiment no. 5, each member of the group is tested for the presence of at least one copy of the G allele of the rs12118655 SNP, wherein a positive test is the presence of at least one copy of the G allele of the rs12118655 SNP.

In a third aspect of embodiment no. 5, each member of the group is tested for the presence at least one copy of the A allele of the rs6679073 SNP, wherein a positive test is the presence of at least one copy of the A allele of the rs6679073 SNP.

In a fourth aspect of embodiment no. 5, each member of the group is tested for the presence at least one copy of the G allele of the rs12564209 SNP, wherein a positive test is the presence of at least one copy of the G allele of the rs12564209 SNP.

In a fifth aspect of embodiment no. 5, each member of the group is tested for the presence at least one copy of the G allele of the rs3805 SNP, wherein a positive test is the presence of at least one copy of the G allele of the rs3805 SNP.

In a sixth aspect of embodiment no. 5, each member of the group is tested for the presence at least one copy of the C allele of the rs71633561 SNP, wherein a positive test is the presence of at least copy of the C allele of the rs71633561 SNP.

In a seventh aspect of embodiment no. 5, each member of the group is tested for the presence at least one copy of the deletion allele of the rs71970505 SNP, wherein a positive test is the presence of at least one copy of the deletion allele of the rs71970505 SNP.

In an eighth aspect of embodiment no. 5, each member of the group is tested for the presence at least one copy of the T allele of the rs12132270 SNP, wherein a positive test is the presence of at least one copy of the T allele of the rs12132270 SNP.

In a ninth aspect of embodiment no. 5, each member of the group is tested for the presence at least one copy of the deletion allele of the rs67625805 SNP, wherein a positive test is the presence of at least one copy of the deletion allele of the rs67625805 SNP.

In a tenth aspect of embodiment no. 5, each member of the group is tested for the presence at least one copy of the A allele of the rs3747972 SNP, wherein a positive test is the presence of at least one copy of the A allele of the rs3747972 SNP.

In an eleventh aspect of embodiment no. 5, each member of the group is tested for the presence at least one copy of the A allele of the rs11557080 SNP, wherein a positive test is the presence of at least one copy of the A allele of the rs11557080 SNP.

In a twelfth aspect of embodiment no. 5, each member of the group is tested for the presence at least one copy of the T allele of the rs71633563 SNP, wherein a positive test is the presence of at least one copy of the T allele of the rs71633563 SNP.

In a thirteenth aspect of embodiment no. 5, each member of the group is tested for the presence at least one copy of the deletion allele of the rs34848415 SNP, wherein a positive test is the presence of at least one copy of the deletion allele of the rs34848415 SNP.

In a fourteenth aspect of embodiment no. 5, each member of the group is tested for the presence at least one copy of the A allele of the rs1891091 SNP, wherein a positive test is the presence of at least one copy of the A allele of the rs1891091 SNP.

In embodiment no. 6, the invention provides a kit for testing a patient having a disease susceptible to treatment with a CRTH2 receptor antagonist for the presence or absence of at least one copy of the better response allele selected from one of the CRTH2 antagonist response markers as set forth in Table 1 above, which comprises a set of oligonucleotides designed to genotype at least one of the CRTH2 antagonist response markers.

In a first aspect of embodiment no. 6, the at least one of the CRTH2 antagonist response markers is the rs12748961 SNP.

In a second aspect of embodiment no. 6, the at least one of the CRTH2 antagonist response markers is the rs12118655 SNP.

In a third aspect of embodiment no. 6, the at least one of the CRTH2 antagonist response markers is the rs6679073 SNP.

In a fourth aspect of embodiment no. 6, the at least one of the CRTH2 antagonist response markers is the rs12564209 SNP.

In a fifth aspect of embodiment no. 6, the at least one of the CRTH2 antagonist response markers is the rs3805 SNP.

In a sixth aspect of embodiment no. 6, the at least one of the CRTH2 antagonist response markers is the rs71633561 SNP.

In a seventh aspect of embodiment no. 6, the at least one of the CRTH2 antagonist response markers is the rs71970505 SNP.

In an eighth aspect of embodiment no. 6, the at least one of the CRTH2 antagonist response markers is the rs12132270 SNP.

In a ninth aspect of embodiment no. 6, the at least one of the CRTH2 antagonist response markers is the rs67625805 SNP.

In a tenth aspect of embodiment no. 6, the at least one of the CRTH2 antagonist response markers is the rs3747972 SNP.

In an eleventh aspect of embodiment no. 6, the at least one of the CRTH2 antagonist response markers is the rs11557080 SNP.

In a twelfth aspect of embodiment no. 6, the at least one of the CRTH2 antagonist response markers is the rs71633563 SNP.

In a thirteenth aspect of embodiment no. 6, the at least one of the CRTH2 antagonist response markers is the rs34848415 SNP.

In a fourteenth aspect of embodiment no. 6, the at least one of the CRTH2 antagonist response markers is the rs1891091 SNP.

In a fifteenth aspect of the kit of embodiment no. 6 (including any one of the first-fourteenth aspects), the oligonucleotides are allele specific oligonucleotide (ASO) probes. In specific aspects, the oligonucleotides are immobilized on a solid surface.

In embodiment no. 7, the invention provides a method of diagnosing a patient who is susceptible to treatment with a CRTH2 receptor antagonist and treating asthma, said method comprising:

(a) obtaining a biological sample (e.g., a blood sample such as a plasma sample) from a human patient;

(b) detecting whether a better response allele of at least one of the CRTH2 receptor antagonist markers in the Table 1 above is present in the blood sample;

(c) diagnosing the patient as susceptible to treatment with a CRTH2 receptor antagonist when the presence of the better response allele in the blood sample is detected; and (d) administering a therapeutically effective amount of a CRTH2 receptor antagonist to the diagnosed patient.

In one aspect of embodiment no. 7, wherein step (d) further comprises administering a leukotriene receptor antagonist to the patient. For example, the leukotriene receptor antagonist can be montelukast or a pharmaceutically acceptable salt thereof.

In one aspect of embodiment no. 7, in step (b), the C allele of the CRTH2 receptor antagonist response marker is rs12748961 SNP is detected, and in step (c), the patient is diagnosed as susceptible to treatment with a CRTH2 receptor antagonist when the C allele of the rs12748961 SNP is detected.

In another aspect of embodiment no. 7, in step (b), the G allele of the CRTH2 receptor antagonist response marker is rs12118655 SNP is detected, and in step (c), the patient is diagnosed as susceptible to treatment with a CRTH2 receptor antagonist when the G allele of the rs12118655 SNP is detected.

In another aspect of embodiment no. 7, in step (b), the A allele of the CRTH2 receptor antagonist response marker is rs6679073 SNP is detected, and in step (c), the patient is diagnosed as susceptible to treatment with a CRTH2 receptor antagonist when the A allele of the rs6679073 SNP is detected.

In another aspect of embodiment no. 7, in step (b), the G allele of the CRTH2 receptor antagonist response marker is rs12564209 SNP is detected, and in step (c), the patient is diagnosed as susceptible to treatment with a CRTH2 receptor antagonist when the G allele of the rs12564209 SNP is detected.

In another aspect of embodiment no. 7, in step (b), the G allele of the CRTH2 receptor antagonist response marker is rs3805 SNP is detected, and in step (c), the patient is diagnosed as susceptible to treatment with a CRTH2 receptor antagonist when the G allele of the rs3805 SNP is detected.

In another aspect of embodiment no. 7, in step (b), the C allele of the CRTH2 receptor antagonist response marker is rs71633561 SNP is detected, and in step (c), the patient is diagnosed as susceptible to treatment with a CRTH2 receptor antagonist when the C allele of the rs71633561 SNP is detected.

In another aspect of embodiment no. 7, in step (b), the deletion allele of the CRTH2 receptor antagonist response marker is rs71970505 SNP is detected, and in step (c), the patient is diagnosed as susceptible to treatment with a CRTH2 receptor antagonist when the deletion allele of the rs71970505 SNP is detected.

In another aspect of embodiment no. 7, in step (b), the T allele of the CRTH2 receptor antagonist response marker is rs12132270 SNP is detected, and in step (c), the patient is diagnosed as susceptible to treatment with a CRTH2 receptor antagonist when the T allele of the rs12132270 SNP is detected.

In another aspect of embodiment no. 7, in step (b), the deletion allele of the CRTH2 receptor antagonist response marker is rs67625805 SNP is detected, and in step (c), the patient is diagnosed as susceptible to treatment with a CRTH2 receptor antagonist when the deletion allele of the rs67625805 SNP is detected.

In another aspect of embodiment no. 7, in step (b), the A allele of the CRTH2 receptor antagonist response marker is rs3747972 SNP is detected, and in step (c), the patient is diagnosed as susceptible to treatment with a CRTH2 receptor antagonist when the A allele of the rs3747972 SNP is detected.

In another aspect of embodiment no. 7, in step (b), the A allele of the CRTH2 receptor antagonist response marker is rs11557080 SNP is detected, and in step (c), the patient is diagnosed as susceptible to treatment with a CRTH2 receptor antagonist when the A allele of the rs11557080 SNP is detected.

In another aspect of embodiment no. 7, in step (b), the T allele of the CRTH2 receptor antagonist response marker is rs71633563 SNP is detected, and in step (c), the patient is diagnosed as susceptible to treatment with a CRTH2 receptor antagonist when the T allele of the rs71633563 SNP is detected.

In another aspect of embodiment no. 7, in step (b), the deletion allele of the CRTH2 receptor antagonist response marker is rs34848415 SNP is detected, and in step (c), the patient is diagnosed as susceptible to treatment with a CRTH2 receptor antagonist when the deletion allele of the rs34848415 SNP is detected.

In another aspect of embodiment no. 7, in step (b), the A allele of the CRTH2 receptor antagonist response marker is rs1891091 SNP is detected, and in step (c), the patient is diagnosed as susceptible to treatment with a CRTH2 receptor antagonist when the A allele of the rs34848415 SNP is detected.

In one aspect of embodiment no. 7, in step (d) the diagnosed patient is administered an effective amount of the CRTH2 receptor antagonist {(7R)-4-fluoro-7-[5-(4-fluorobenzyl)-1H-[1,2,3]triazol-1-yl]-6,7,8,9-tetrahydropyrido[1,2-a]indol-10-yl}-acetic acid and the leukotriene receptor antagonist montelukast.

In one particular aspect of embodiment no. 7, in step (b), the better response allele that is sought to be detected is the C allele of the CRTH2 receptor antagonist response marker is rs12748961 SNP;

in step (c), the patient is diagnosed as susceptible to treatment with a CRTH2 receptor antagonist when the C allele of the rs12748961 SNP is detected; and in step (d), the diagnosed patient is administered an effective amount of the CRTH2 receptor antagonist {(7R)-4-fluoro-7-[5-(4-fluorobenzyl)-1H-[1,2,3]triazol-1-yl]-6,7,8,9-tetrahydropyrido[1,2-a]indol-10-yl}-acetic acid and the leukotriene receptor antagonist montelukast.

In embodiment no. 8, the invention provides for the (i) method of embodiment no. 1, (ii) drug product of embodiment no. 2, (iii) use of embodiment no. 3, (iv) method of embodiment no. 4, (v) method of embodiment no. 5, a (vi) kit of embodiment no. 6, or a method of embodiment no. 7; wherein the patient is susceptible to treatment with a CRTH2 receptor antagonist has a positive test for at least one copy of the better response allele for at least two of the CRTH2 receptor antagonist markers in Table 1 above. For example, in this embodiment, the patient susceptible to treatment with a CRTH2 receptor antagonist is identified where patients have both at least one copy of the C allele of the rs12748961 SNP and at least one copy of the G allele of the rs12118655 SNP.

In certain embodiments of the methods, uses, drug products, or kits described in the embodiments above, the CRTH2 receptor antagonist is {(7R)-4-fluoro-7-[5-(4-fluorobenzyl)-1H-[1,2,3]triazol-1-yl]-6,7,8,9-tetrahydropyrido[1,2-a]indol-10-yl}-acetic acid or 2-(2-methyl-1-(4-(methylsulfonyl)-2-(trifluoromethyl)benzyl)-1H-pyrrolo[2,3-b]pyridin-3-yl)acetic acid (fevipiprant), or a pharmaceutically acceptable salt of either compound.

In certain embodiments of the methods, uses, drug products, or kits described in the embodiments above, the disorder susceptible to treatment with a CRTH2 receptor antagonist is asthma.

BRIEF DESCRIPTION OF THE DRAWINGS

FIG. 1 shows reference nucleotide sequences for the CRTH2 antagonist response markers with the variant position indicated in bold font in the NCBI SNP database as of Jun. 7, 2015.

DETAILED DESCRIPTION OF THE INVENTION

I. Definitions

Figure 2:
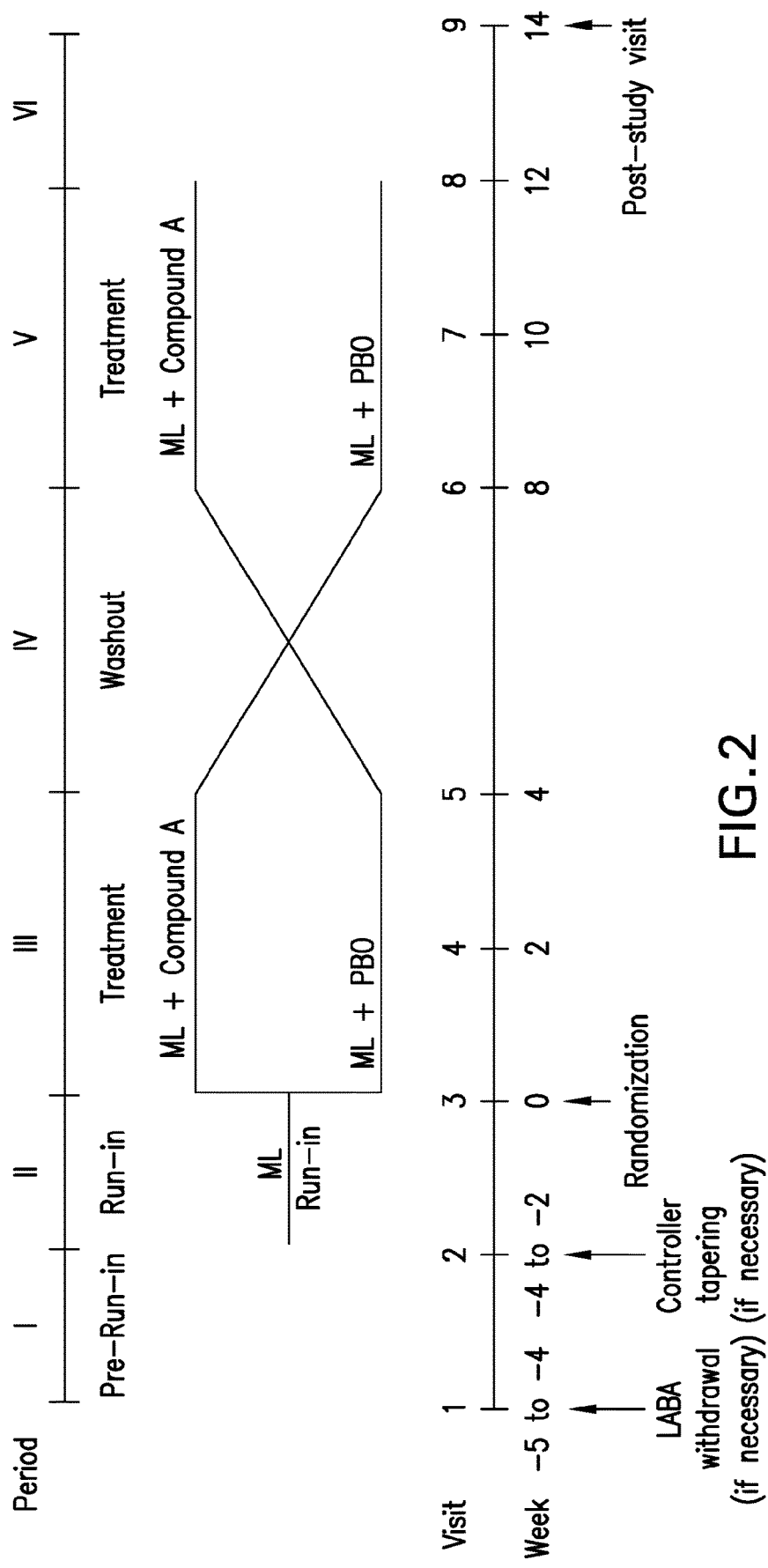
FIG. 2 is graphical depiction of a study design used in measuring the efficacy of patients treated with a CRTH2 receptor antagonist and montelukast.

So that the invention may be more readily understood, certain technical and scientific terms are specifically defined below. Unless specifically defined elsewhere in this document, all other technical and scientific terms used herein have the meaning that would be commonly understood by one of ordinary skill in the art to which this invention belongs when used in similar contexts as used herein.

As used herein, including the appended claims, the singular forms of words such as "a," "an," and "the," include their corresponding plural references unless the context clearly dictates otherwise.

"About" when used to modify a numerically defined parameter, e.g., the dosage for a therapeutic agent discussed herein, or the length of treatment time, means that the parameter may vary by as much as 10% above or below the stated numerical value for that parameter.

"Allele" is a particular form of a gene or other genetic locus, distinguished from other forms by its particular nucleotide sequence, the term allele also includes one of the alternative polymorphisms (e.g., a SNP) found at a polymorphic site.

"Beneficial result" means a desired clinical result of treatment with a CRTH2 receptor antagonist, including but not limited to: alleviation of one or more disease symptoms, diminishment of extent of disease (e.g., improvement in $FEV_1$ in the context of the treatment of asthma), stabilized (i.e., not worsening) state of disease, slowing of disease progression, amelioration or palliation of a disease state, prolonging survival (as compared to expected survival if not treated), relapse-free survival, remission (whether partial or total) and cure (i.e., elimination of the disease).

"Better response allele" is the particular form of a gene or other genetic locus, where if present in a patient, results in an improved clinical measure (e.g., an improved $FEV_1$ measure) as compared to the measure in a patient where such form of the gene or other genetic locus is absent.

"Consists essentially of" and variations such as "consist essentially of" or "consisting essentially of" as used throughout the specification and claims, indicate the inclusion of any recited elements or group of elements, and the optional inclusion of other elements, of similar or different nature than the recited elements, which do not materially change the basic or novel properties of the specified dosage regimen, method, or composition.

"Individual" or "animal" or "patient" or "mammal," is meant any human subject, particularly a mammalian subject, for whom any of the claimed compositions and methods is needed or may be beneficial. In preferred embodiments, the individual is an adult human, i.e., at least 18 years of age.

"Isolated" is typically used to reflect the purification status of a biological molecule such as RNA, DNA, oligonucleotide, or protein, and in such context means the molecule is substantially free of other biological molecules such as nucleic acids, proteins, lipids, carbohydrates, or other material such as cellular debris and growth media. Generally, the term "isolated" is not intended to refer to a complete absence of other biological molecules or material or to an absence of water, buffers, or salts, unless they are present in amounts that substantially interfere with the methods of the present invention.

"Locus" refers to a location on a chromosome or DNA molecule corresponding to a gene, a physical feature such as a polymorphic site, or a location associated with a phenotypic feature.

"Nucleotide pair" is the set of two nucleotides (which may be the same or different) found at a polymorphic site on the two copies of a chromosome from an individual.

"Oligonucleotide" refers to a nucleic acid that is usually between 5 and 100 contiguous bases in length, and most frequently between 10-50, 10-40, 10-30, 10-25, 10-20, 15-50, 15-40, 15-30, 15-25, 15-20, 20-50, 20-40, 20-30 or 20-25 contiguous bases in length. The sequence of an oligonucleotide can be designed to specifically hybridize to any of the allelic forms of a locus; such oligonucleotides are referred to as allele-specific probes. If the locus is a PS comprising a SNP, the complementary allele for that SNP can occur at any position within an allele-specific probe. Other oligonucleotides useful in practicing the invention specifically hybridize to a target region adjacent to a PS with their 3' terminus located one to less than or equal to about 10 nucleotides from the PS, preferably about 5 nucleotides. Such oligonucleotides hybridizing adjacent to a PS are useful in polymerase-mediated primer extension methods and are referred to herein as "primer-extension oligonucleotides". In a preferred embodiment, the 3'-terminus of a primer-extension oligonucleotide is a deoxynucleotide complementary to the nucleotide located immediately adjacent to the PS.

"Pharmaceutically acceptable" refers to molecular entities and compositions that are "generally regarded as safe"—e.g., that are physiologically tolerable and do not typically produce an allergic or similar untoward reaction, such as gastric upset and the like, when administered to a human. In another embodiment, this term refers to molecular entities and compositions approved by a regulatory agency of the federal or a state government or listed in the U.S. Pharmacopeia or another generally recognized pharmacopeia for use in animals, and more particularly in humans.

"Polymorphic site" or "PS" refers to the position in a genetic locus or gene at which a polymorphism is found, e.g., single nucleotide polymorphism (SNP), restriction fragment length polymorphism (RFLP), variable number of tandem repeat (VNTR), dinucleotide repeat, trinucleotide repeat, tetranucleotide repeat, simple sequence repeat, insertion element such as Alu, and deletion or insertion of one or more nucleotides. A PS is usually preceded by and followed by highly conserved sequences in the population of interest and thus the location of a PS is typically made in reference to a consensus nucleic acid sequence of thirty to sixty nucleotides that bracket the PS, which in the case of a SNP is commonly referred to as the "SNP context sequence". The location of the PS may also be identified by its location in a consensus or reference sequence. The skilled artisan understands that the location of a particular PS may not occur at precisely the same position in a reference or context sequence in each individual in a population of interest due to the presence of one or more insertions or deletions in that individual as compared to the consensus or reference sequence. Moreover, it is routine for the skilled artisan to design robust, specific and accurate assays for detecting the alternative alleles at a polymorphic site in any given individual, when the skilled artisan is provided with the identity of the alternative alleles at the PS to be detected and one or both of a reference sequence or context sequence in which the PS occurs. Thus, the skilled artisan will understand that specifying the location of any PS described herein by reference to a particular position in a reference or context sequence is merely for convenience and that any specifically enumerated nucleotide position literally includes whatever nucleotide position the same PS is actually located at in the same locus in any individual being tested for the presence or absence of a genetic marker of the invention using any of the genotyping methods described herein or other genotyping methods well-known in the art.

"Reference SNP" or "rs" number refers to an accession number assigned to an individual SNP by the National Center for Biotechnology Information (NCBI).

"Treat" or "Treating" means to administer a therapeutic agent, such as a composition containing CRTH2 receptor antagonists described herein, internally or externally to an individual in need of the therapeutic agent. Individuals in need of the agent include individuals who have been diagnosed as having, or at risk of developing, a condition or disorder susceptible to treatment with the agent, as well as individuals who have, or are at risk of developing, one or more adverse effects of treatment with a first therapeutic agent that are susceptible to alleviation with a second therapeutic agent. Typically, the therapeutic agent is administered in a therapeutically effective amount, which means an amount effective to produce one or more beneficial results. The therapeutically effective amount of a particular agent may vary according to factors such as the disease state, age, and weight of the patient being treated, and the sensitivity of the patient, e.g., ability to respond, to the therapeutic agent. Whether a beneficial or clinical result has been achieved can be assessed by any clinical measurement typically used by physicians or other skilled healthcare providers to assess the presence, severity or progression status of the targeted disease, symptom or adverse effect. Typically, a therapeutically effective amount of an agent will result in an improvement in the relevant clinical measurement(s) over the baseline status, or over the expected status if not treated, of at least 5%, usually by at least 10%, more usually at least 20%, most usually at least 30%, preferably at least 40%, more preferably at least 50%, most preferably at least 60%, ideally at least 70%, more ideally at least 80%, and most ideally at least 90%. For instance, in one embodiment wherein the condition or disorder is asthma, a clinical measure of improvement is an improvement in the $FEV_1$ measure. While an embodiment of the present invention (e.g., a treatment method or article of manufacture) may not achieve the desired clinical benefit or result in every patient, it should do so in a statistically significant number of patients as determined by any statistical test known in the art such as the Student's t-test, the chi$^2$-test, the U-test according to Mann and Whitney, the Kruskal-Wallis test (H-test), Jonckheere-Terpstra-test and the Wilcoxon-test.

II. Utility of CRTH2 Antagonist Response Marker of the Invention

The phenotypic effect of the response marker described herein supports the use of this marker in a variety of commercial applications, including but not limited to, clinical trials of investigational or previously approved CRTH2 receptor antagonist drugs in patients selected on the basis of the presence or absence of this response marker, pharmaceutical compositions and drug products comprising a CRTH2 receptor antagonist for treating patients who have this response marker, diagnostic methods, and pharmacogenetic treatment methods, which involve tailoring a patient's drug therapy based on whether the patient has this marker.

The utility of any of the commercial applications claimed herein does not require that the correlation between the presence of a response marker of the invention and the occurrence of the desired response to the CRTH2 receptor antagonist be observed in 100% of the individuals that receive the CRTH2 receptor antagonist; nor does it require a diagnostic method or kit to have a specific degree of specificity or sensitivity in determining the presence or absence of the response marker in every individual, nor does it require that a diagnostic method claimed herein be 100% accurate in predicting for every individual whether the individual is likely to have a beneficial response to a CRTH2 receptor antagonist. Thus, the inventors herein intend that the terms "determine", "determining" and "predicting" should not be interpreted as requiring a definite or certain result; instead these terms should be construed as meaning that a claimed method provides an accurate result for the majority of individuals, or that the result or prediction for any given individual is more likely to be correct than incorrect.

Preferably, the accuracy of the result provided by a diagnostic method of the invention is one that a skilled artisan or regulatory authority would consider suitable for the particular application in which the method is used. Similarly, the utility of the claimed drug products and treatment methods does not require that they produce the claimed or desired effect in every individual; all that is required is that a clinical practitioner, when applying his or her professional judgment consistent with all applicable norms, decides that the chance of achieving the claimed effect of treating a given individual according to the claimed method or with the claimed drug product is sufficiently high to warrant prescribing the treatment or drug product.

A. Testing for a CRTH2 Antagonist Response Marker of the Invention

The presence or absence of the CRTH2 antagonist response markers may be detected by any of a variety of genotyping techniques commonly used in the art. Typically, such genotyping techniques employ one or more oligonucleotides that are complementary to a region containing, or adjacent to, the PS of interest. The sequence of an oligonucleotide used for genotyping a particular PS of interest is typically designed based on a context sequence for the PS.

The location, in a particular individual, of the polymorphic site identified above is in a reference coding or genomic DNA sequence surrounding the PS of interest or in one of the context sequences described in Table 2 below, or their complementary sequences.

TABLE 2

Context sequences for SNPs associated with CRTH2 Receptor Antagonist Response

| PS | Short Context Sequences[1] | SEQ ID NO: |
|---|---|---|
| rs12748961 | CTCTTCACTATGTTGAAATTGGGTCY[1]TTCTTCCC CAAAGATTGAAGAGAAT | 1 |
| rs12118655 | TCAGATGGGAAATATTGCAGGGGCTY[2]TATGGT CTCCATCGCAACTACTCAC | 2 |
| rs6679073 | TTTTGAGACTGGCAAATGTTCTGCAY[3]CCAGTAT CTGCTCAATACTTTTGTG | 3 |
| rs12564209 | CAAAAGTCTTTAGGATAGTCTCTGGY[4]TCACAGT AAGTGCTACGTAAGTGTT | 4 |
| rs3805 | TTTTTATACATGTTATTTTAGGGCAY[5]AAGCTGA GTACTATACCCCCACACC | 5 |
| rs71633561 | GAGGTAGGAGAATCACTTGAACCCAY[6]GGGTCA GAGGTTGTGGTGAGCCGAG | 6 |
| rs71970505 | AGTTTGCAAAGTAACCCATTTGGCCY[7]AAGTCAT ACAACTCTAGAGGGACAA | 7 and 14 (-allele) |
| rs12132270 | CTCCTATCTCCATTTTACTCTTATGY[8]CTACCCCC AGAATAGGTTTTCTGGA | 8 |
| rs67625805 | GGTGGTAATGTATATTTATCTTAAAY[9]TTTTTTTT TTTTTTTGAGACGGAGT | 9 |
| rs3747972 | GCGGATCGCCTGAGATCAGGAGTTCY[10]AGACCA GCCTGGCCAACATGGTGAA | 10 |
| rs11557080 | CGCAATGGTGTGATCTCAGCTCACTY[11]CAACCT CTAACTCCCAGGTTCAAGC | 11 |
| rs71633563 | CTGCCTACAAAAGTATCAGGCAAGAY[12]AGGCCT CACGTTAGATGAGATAGTA | 12 |
| rs34848415 | GGCAATAAGAGTGAAACTCCATCTCY[13]AAAAA AAAAAAAAAAAATCTATTT | 13 |
| rs1891091 | ACCTCCTCCCATAAATTGCAGAATCY[15]ATTCCCT TCCTGCCCACTCTCAGTG | 15 |

[1]Context sequence reported in NCBI SNP Database on Jun. 23, 2016;
Y[1] indicates C or T
Y[2] indicates A or G;
Y[3] indicates A or C;
Y[4] indicates C or G;
Y[5] indicates A/G/T;
Y[6] indicates C or G;
Y[7] indicates the absence (-) or presence of ATGCAGACTGT;
Y[8] indicates C or T;
Y[9] indicates the absence (-) or presence of T;
Y[10] indicates A or G;
Y[11] indicates A or G;
Y[12] indicates C or T;
Y[13] indicates the absence (-) or presence of A, and
Y[15] indicates A or G.

As recognized by the skilled artisan, nucleic acid samples containing a particular PS may be complementary double stranded molecules and thus reference to a particular site on the sense strand refers as well to the corresponding site on the complementary antisense strand. Similarly, reference to a particular genotype obtained for a PS on both copies of one strand of a chromosome is equivalent to the complementary genotype obtained for the same PS on both copies of the other strand. By way of example, a C/C genotype for the rs12748961 PS on the coding strand for the gene is equivalent to a G/G genotype for that PS on the noncoding strand.

The context sequences recited herein, as well as their complementary sequence, may be used to design probes and primers for genotyping the CRTH2 antagonist response markers in a nucleic acid sample obtained from a human subject of interest using any of a variety of methods well known in the art that permits the determination of whether the individual has at least one copy for the better response allele. Nucleic acid molecules utilized in such methods generally include RNA, genomic DNA, or cDNA derived from RNA.

Typically, genotyping methods involve assaying a nucleic acid sample prepared from a biological sample obtained from the individual to determine the identity of a nucleotide or nucleotide pair present at one or more polymorphic sites of interest. Nucleic acid samples may be prepared from virtually any biological sample. For example, convenient samples include whole blood serum, semen, saliva, tears, fecal matter, urine, sweat, buccal matter, skin and hair. Somatic cells are preferred since they allow the determination of the identity of both alleles present at the PS of interest.

Nucleic acid samples may be prepared for analysis using any technique known to those skilled in the art. Preferably, such techniques result in the isolation of genomic DNA sufficiently pure for determining the genotype for the desired polymorphic site(s) in the nucleic acid molecule. To enhance the sensitivity and specificity of that determination, it is frequently desirable to amplify from the nucleic acid sample a target region containing the PS to be genotyped. Nucleic acid isolation and amplification techniques may be found, for example, in Sambrook, et al., Molecular Cloning: A Laboratory Manual (Cold Spring Harbor Laboratory, New York) (2001).

Any amplification technique known to those of skill in the art may be used in practicing the present invention including, but not limited to, polymerase chain reaction (PCR) techniques. PCR may be carried out using materials and methods known to those of skill in the art (See generally PCR Technology: Principals and Applications for DNA Amplification (ed. H. A. Erlich, Freeman Press, NY, N.Y., 1992); PCR Protocols: A Guide to Methods and Applications (eds. Innis, et al., Academic Press, San Diego, Calif., 1990); Matilla et al., *Nucleic Acids Res.* 19: 4967 (1991); Eckert et al., PCR Methods and Applications 1: 17 (1991); PCR (eds. McPherson et al., IRL Press, Oxford); and U.S. Pat. No. 4,683,202. Other suitable amplification methods include the ligase chain reaction (LCR) (see Wu and Wallace, *Genomics* 4: 560 (1989) and Landegren et al., *Science* 241: 1077 (1988)), transcription amplification (Kwoh et al., *Proc. Natl. Acad. Sci. USA* 86: 1173 (1989)), self-sustained sequence replication (Guatelli et al., *Proc. Nat. Acad. Sci. USA*, 87: 1874 (1990)); isothermal methods (Walker et al., *Proc. Natl. Acad. Sci. USA* 89:392-6 (1992)); and nucleic acid-based sequence amplification (NASBA).

The amplified target region is assayed to determine the identity of at least one of the alleles present at a PS in the target region. If both alleles of a locus are represented in the amplified target, it will be readily appreciated by the skilled artisan that only one allele will be detected at a PS in individuals who are homozygous at that PS, while two different alleles will be detected if the individual is heterozygous for that PS.

The identity of the allele may be identified directly, known as positive-type identification, or by inference, referred to as negative-type identification. For example, where a SNP is known to be guanine or cytosine in a reference population, a PS may be positively determined to be either guanine or cytosine for an individual homozygous at that site, or both guanine and cytosine, if the individual is heterozygous at that site. Alternatively, the PS may be negatively determined to be not guanine (and thus cytosine/cytosine) or not cytosine (and thus guanine/guanine). In either case, where it is determined that at least one copy of a better response allele is present as set forth in Table 1, that determination is deemed to be a positive test result for the better response allele in the methods, uses, drug products, or kits described herein.

Identifying the allele or pair of alleles (e.g., the two nucleotides in case of a SNP) at a PS in a nucleic acid sample obtained from an individual may be accomplished using any technique known to those of skill in the art. Preferred techniques permit rapid, accurate assaying of multiple PS with a minimum of sample handling. Some examples of suitable techniques include, but are not limited to, direct DNA sequencing of the amplified target region, capillary electrophoresis, hybridization of allele-specific probes, single-strand conformation polymorphism analysis, denaturing gradient gel electrophoresis, temperature gradient electrophoresis, mismatch detection; nucleic acid arrays, primer specific extension, protein detection, and other techniques well known in the art. See, for example, Sambrook, et al., Molecular Cloning: A Laboratory Manual (Cold Spring Harbor Laboratory, New York) (2001); Ausubel, et al., Current Protocols in Molecular Biology (John Wiley and Sons, New York) (1997); Orita et al., *Proc. Nat. Acad. Sci. USA* 86, 2766-2770 (1989); Humphries et al., in MOLECULAR DIAGNOSIS OF GENETIC DISEASES, Elles, ed., pp. 321-340, 1996; Wartell et al., *Nucl. Acids Res.* 18:2699-706 (1990); Hsu et al. (1994) *Carcinogenesis* 15:1657-1662; Sheffield et al., *Proc. Natl. Acad. Sci. USA* 86:232-6 (1989); Winter et al., *Proc. Natl. Acad. Sci. USA* 82:7575 (1985); Myers et al. (1985) *Nature* 313:495; Rosenbaum and Reissner (1987) *Biophys Chem.* 265:12753; Modrich, *Ann. Rev. Genet.* 25:229-53 (1991); U.S. Pat. Nos. 6,300,063; 5,837, 832; 5,459,039; and HuSNP Mapping Assay, reagent kit and user manual, Affymetrix Part No. 90094 (Affymetrix, Santa Clara, Calif.).

In preferred embodiments, the identity of the allele(s) at a PS is determined using a polymerase-mediated primer extension method. Several such methods have been described in the patent and scientific literature and include the "Genetic Bit Analysis" method (WO 92/15712) and the ligase/polymerase mediated genetic bit analysis (U.S. Pat. No. 5,679,524. Related methods are disclosed in WO 91/02087, WO 90/09455, WO 95/17676, and U.S. Pat. Nos. 5,302,509 and 5,945,283. Extended primers containing the complement of the polymorphism may be detected by mass spectrometry as described in U.S. Pat. No. 5,605,798.

Another primer extension method employs allele specific PCR (Ruano, G. et al., *Nucl. Acids Res.* 17:8392 (1989); Ruano, G. et al., *Nucl. Acids Res.* 19:6877-82 (1991); WO 93/22456; Turki et al., *J. Gun. Invest.* 95:1635-41 (1995)).

Yet another primer extension method for identifying and analyzing polymorphisms utilizes single-base extension (SBE) of a fluorescently-labeled primer coupled with fluorescence resonance energy transfer (FRET) between the label of the added base and the label of the primer. Typically, the method, such as that described by Chen et al., *Proc. Nat. Acad. Sci.* 94:10756-61 (1997) uses a locus-specific oligonucleotide primer labeled on the 5' terminus with 5-carboxyfluorescein (FAM). This labeled primer is designed so that the 3' end is immediately adjacent to the polymorphic site of interest. The labeled primer is hybridized to the locus, and single base extension of the labeled primer is performed with fluorescently labeled dideoxyribonucleotides (ddNTPs) in dye-terminator sequencing fashion, except that no deoxyribonucleotides are present. An increase in fluorescence of the added ddNTP in response to excitation at the wavelength of the labeled primer is used to infer the identity of the added nucleotide.

A preferred genotyping assay is a TaqMan® SNP Genotyping Assay from Thermo Fisher Scientific, Waltham, Mass., USA, or an assay having about the same reliability, accuracy and specificity. In certain embodiments of such an assay, two allele-specific probes are used to target a specific PS, with each probe having a distinct fluorescent label bonded to it as well as a quencher molecule. In addition, two allele-specific primers are used. Upon extension of the DNA strand, the Taq DNA polymerase cleaves the fluorescent label which cleavage results in fluorescence emissions which can be detected.

In all of the above methods, the accuracy and specificity of an assay designed to detect the identity of the allele(s) at any PS is typically validated by performing the assay on DNA samples in which the identity of the allele(s) at that PS is known. Preferably, a sample representing each possible allele is included in the validation process. For diploid loci such as those on autosomal chromosomes, the validation samples will typically include a sample that is homozygous for the major allele at the PS, a sample that is homozygous for the minor allele at the PS, and a sample that is heterozygous at that PS. These validation samples are typically also included as controls when performing the assay on a test sample (i.e., a sample in which the identity of the allele(s) at the PS is unknown). The specificity of an assay may also be confirmed by comparing the assay result for a test sample with the result obtained for the same sample using a different type of assay, such as by determining the sequence of an amplified target region believed to contain the PS of interest and comparing the determined sequence to context sequences accepted in the art, such as the context sequences provided herein.

The length of the context sequence necessary to establish that the correct genomic position is being assayed will vary based on the uniqueness of the sequence in the target region (for example, there may be one or more highly homologous sequences located in other genomic regions). The skilled artisan can readily determine an appropriate length for a context sequence for any PS using known techniques such as BLASTing the context sequence against publicly available sequence databases. For amplified target regions, which provide a first level of specificity, examining the context sequence of about 30 to 60 bases on each side of the PS in known samples is typically sufficient to ensure that the assay design is specific for the PS of interest. Occasionally, a validated assay may fail to provide an unambiguous result for a test sample. This is usually the result of the sample having DNA of insufficient purity or quantity, and an unambiguous result is usually obtained by repurifying or reisolating the DNA sample or by assaying the sample using a different type of assay.

For detecting PS characterized by an insertion/deletion variations, a number of assay techniques can be employed. Insertion/deletion variants can be detected by Sanger sequencing methods which employ di-deoxynucleosidetriphosphates. In some embodiments, commercially available software packages such as Mutation Surveyor® software available from SoftGenetics LLC, State College, Pa., USA that can detect homozygous and heterozygous insertion/deletion variants. In addition, the fragment analysis method disclosed in Hjelm et al. in *The Journal of Molecular Diagnostics* 12(5), pp 607-610 (2010) can be used to characterize insertion and deletion variants.

Programs such as Variant Caller with Multinomial Probabilistic Mode as disclosed in *Scientific Reports*, 3, 2161 (2013) and at http://emu.src.riken.jp/VCMM/ can be used to detect insertion/deletion variants with high accuracy. Another method for the detection of insertion/deletion variants is disclosed in Z. Yhang et al., *Nucleic Acids Research* 43(9) 349 (2015), which relies on amplicon labeling and automated capillary electrophoresis.

Further, in performing any of the methods described herein that require determining the presence or absence of the CRTH2 antagonist response markers, such determination may be made by consulting a data repository that contains sufficient information on the patient's genetic composition to determine whether the patient has the marker. Preferably, the data repository lists whether the CRTH2 antagonist response markers are present and absent in the individual. The data repository could include the individual's patient records, a medical data card, a file (e.g., a flat ASCII file) accessible by a computer or other electronic or non-electronic media on which appropriate information or genetic data can be stored. As used herein, a medical data card is a portable storage device such as a magnetic data card, a smart card, which has an on-board processing unit and which is sold by vendors such as Siemens of Munich Germany, or a flash-memory card. If the data repository is a file accessible by a computer; such files may be located on various media, including: a server, a client, a hard disk, a CD, a DVD, a personal digital assistant such as a smart phone, a tape, a zip disk, the computer's internal ROM (read-only-memory) or the internet or worldwide web. Other media for the storage of files accessible by a computer will be obvious to one skilled in the art.

The invention also contemplates that testing for the CRTH2 antagonist response markers may be determined by investigating whether the individual has an allele, e.g., a particular nucleotide sequence, at a different locus that is in high linkage disequilibrium (LD) with the better response allele for the rs12748961 SNP or one of the other CRTH2 antagonist response markers identified in Table 1 above. Two particular alleles at different loci on the same chromosome are said to be in LD if the presence of one of the alleles at one locus tends to predict the presence of the other allele at the other locus. Such variants, which are referred to herein as linked variants, or proxy variants, may be any type of variant (e.g., a SNP, insertion or deletion variant) that is in high LD with the better response allele of interest.

Linked variants are readily identified by determining the degree of linkage disequilibrium (LD) between the better response allele of the rs12748961 SNP, for example, and a candidate linked allele. The candidate linked variant may be an allele of a polymorphism that is currently known. Other candidate linked variants may be readily identified by the skilled artisan using any technique well-known in the art for discovering polymorphisms.

The degree of LD between a better response allele in one of the CRTH2 antagonist response markers, e.g., the rs12748961 SNP, and a candidate linked variant may be determined using any LD measurement known in the art. LD patterns in genomic regions are readily determined empirically in appropriately chosen samples using various techniques known in the art for determining whether any two alleles (e.g., between nucleotides at different PSs) are in linkage disequilibrium (see, e.g., GENETIC DATA ANALYSIS II, Weir, Sineuer Associates, Inc. Publishers, Sunderland, Mass. 1996). The skilled artisan may readily select which method of determining LD will be best suited for a particular population sample size and genomic region. One of the most frequently used measures of linkage disequilibrium is $r^2$, which is calculated using the formula described by Devlin et al. (*Genomics*, 29(2):311-22 (1995)). $r^2$ is the measure of how well an allele X at a first locus predicts the occurrence of an allele Y at a second locus on the same chromosome. The measure only reaches 1.0 when the prediction is perfect (e.g., X if and only if Y).

In one embodiment, the locus of the linked variant is in a genomic region of about 100 kilobases, more preferably about 10 kb that spans any of the PS of the rs12748961 SNP. Other linked variants are those in which the LD with the better response allele has a $r^2$ value, as measured in a suitable reference population, of at least 0.75, more preferably at least 0.80, even more preferably at least 0.85 or at least 0.90, yet more preferably at least 0.95, and most preferably 1.0. The reference population used for this $r^2$ measurement may be the general population, a population using the CRTH2 receptor antagonist, a population diagnosed with a particular condition for which the CRTH2 receptor antagonist shows efficacy or a population whose members are self-identified as belonging to the same ethnic group, such as Caucasian, African American, Hispanic, Latino, Native American and the like, or any combination of these categories. Preferably the reference population reflects the genetic diversity of the population of patients to be treated with a CRTH2 receptor antagonist.

In some embodiments such as the r2 in reported in Table 6 in Example 2, the r2 is the Pearson correlation coefficient squared, where the Pearson correlation coefficient is calculated from the genotype data (numerically coded as 0, 1, 2 being the number of minor alleles of each variant for each subject) between each variant and rs12748961. r2 ranges from 0 to 1, with 1 representing two perfectly correlated variants and 0 representing two independent variants (based on the analysis dataset).

In some embodiments, a physician determines whether a patient has the CRTH2 receptor antagonist response marker described herein by ordering a diagnostic test, which is designed to determine whether the patient has at least one copy of the better response allele of one of the CRTH2 antagonist response markers in Table 1, e.g., the rs12748961 SNP. Preferably the test determines the identity of both alleles, i.e., the genotype, at this PS. In some embodiments, the testing laboratory will prepare a nucleic acid sample from a biological sample (such as a blood sample or buccal swab) obtained from the patient. In some embodiments, a blood sample from the patient is drawn by the physician or a member of the physician's staff, or by a technician at a diagnostic laboratory. In some embodiments, the patient is provided with a kit for taking a buccal swab from the inside of her cheek, which the patient then gives to the physician's staff member or sends directly to the diagnostic laboratory.

In some embodiments, the testing laboratory does not know the identity of the individual whose sample it is testing; i.e., the sample received by the laboratory is made anonymous in some manner before being sent to the laboratory. For example, the sample may be merely identified by a number or some other code (a "sample ID") and the results of the diagnostic method can be reported to the party ordering the test using the sample ID.

In some embodiments, after the test results have been obtained, the testing laboratory generates a test report which indicates whether the better response allele is present or absent at the genotyped polymorphic site, and preferably indicates whether the patient is heterozygous or homozygous for the better response allele. In some embodiments, the test report is a written document prepared by the testing laboratory and sent to the patient or the patient's physician as a hard copy or via electronic mail. In other embodiments, the test report is generated by a computer program and displayed on a video monitor in the physician's office. The test report may also comprise an oral transmission of the test results directly to the patient or the patient's physician or an authorized employee in the physician's office. Similarly, the test report may comprise a record of the test results that the physician makes in the patient's file.

In one embodiment, if the patient tests positive for at least one copy of the better response allele, then the test report further indicates that the patient tested positive for a genetic marker associated with a likely response to treatment with a CRTH2 antagonist, while if the individual tests negative for the better response allele, then the test report further indicates that the patient tested negative for a genetic marker associated with a likely response to treatment with a CRTH2 antagonist.

Typically, the individual would be tested for the presence of a CRTH2 receptor antagonist response marker prior to initiation of the CRTH2 receptor antagonist therapy, but it is envisioned that such testing could be performed at any time after the individual is administered the first dose of a CRTH2 receptor antagonist. For example, the treating physician may be concerned that the patient has not responded adequately and desires to test the individual to determine whether continued treatment with the CRTH2 receptor antagonist is warranted. In some embodiments, a physician may determine whether or not an individual should be tested for a CRTH2 receptor antagonist response marker. For example, the physician may be considering whether to prescribe for the patient a pharmaceutical product that is indicated for patients who test positive for the CRTH2 receptor antagonist response marker.

In deciding how to use the CRTH2 receptor antagonist response marker test results in treating any individual patient, the physician may also take into account other relevant circumstances, such as the disease or condition to be treated, the age, weight, gender, genetic background and race of the patient, including inputting a combination of these factors and the genetic marker test results into a model that helps guide the physician in choosing a therapy and/or treatment regimen with that therapy.

Detecting the presence or absence of any of the CRTH2 receptor antagonist response markers may be performed using a kit that has been specially designed for this purpose. In one embodiment, a kit of the invention comprises a set of oligonucleotides designed for identifying each of the alleles at the PS, e.g., in rs12748961.

In some embodiments, the oligonucleotides in the kit are either allele-specific probes or allele-specific primers. In other embodiments, the kit comprises primer-extension oligonucleotides. In still further embodiments, the set of oligonucleotides is a combination of allele-specific probes, allele-specific primers and primer-extension oligonucleotides. The kit may comprise oligonucleotides designed for detecting the presence of other genetic markers associated with response to CRTH2 receptor antagonist therapy.

Oligonucleotides in kits of the invention must be capable of specifically hybridizing to a target region of a polynucleotide. As used herein, specific hybridization means the oligonucleotide forms an anti-parallel double-stranded structure with the target region under certain hybridizing conditions, while failing to form such a structure with non-target regions when incubated with the polynucleotide under the same hybridizing conditions. In some embodiments, the target region contains the PS of interest, while in other embodiments, the target region is located one to 10 nucleotides adjacent to the PS.

The composition and length of each oligonucleotide in the kit will depend on the nature of the genomic region containing the PS as well as the type of assay to be performed with the oligonucleotide and is readily determined by the skilled artisan.

For example, the polynucleotide to be used in the assay may constitute an amplification product, and thus the required specificity of the oligonucleotide is with respect to hybridization to the target region in the amplification product rather than in genomic or cDNA isolated from the individual. As another example, if the kit is designed to genotype two or more polymorphic sites simultaneously, the melting temperatures for the oligonucleotides for each PS in the kit will typically be within a narrow range, preferably less than about 5° C. and more preferably less than about 2° C.

In some embodiments, each oligonucleotide in the kit is a perfect complement of its target region. An oligonucleotide is said to be a "perfect" or "complete" complement of another nucleic acid molecule if every nucleotide of one of the molecules is complementary to the nucleotide at the corresponding position of the other molecule. While perfectly complementary oligonucleotides are preferred for detecting polymorphisms, departures from complete complementarity are contemplated where such departures do not prevent the molecule from specifically hybridizing to the target region as defined above. For example, an oligonucleotide primer may have a non-complementary fragment at its 5' end, with the remainder of the primer being completely complementary to the target region. Alternatively, non-complementary nucleotides may be interspersed into the probe or primer as long as the resulting probe or primer is still capable of specifically hybridizing to the target region.

In some preferred embodiments, each oligonucleotide in the kit specifically hybridizes to its target region under stringent hybridization conditions. Stringent hybridization conditions are sequence-dependent and vary depending on the circumstances. Generally, stringent conditions are selected to be about 5° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. As the target sequences are generally present in excess, at Tm, 50% of the probes are occupied at equilibrium.

Typically, stringent conditions include a salt concentration of at least about 0.01 to 1.0 M sodium ion concentration (or other salts) at pH 7.0 to 8.3 and the temperature is at least about 25° C. for short oligonucleotide probes (e.g., 10 to 50 nucleotides). Stringent conditions can also be achieved with the addition of destabilizing agents such as formamide. For example, conditions of 5×SSPE (750 mM NaCl, 50 mM NaPhosphate, 5 mM EDTA, pH 7.4) and a temperature of 25-30° C. are suitable for allele-specific probe hybridizations. Additional stringent conditions can be found in Molecular Cloning: A Laboratory Manual, Sambrook et al., Cold Spring Harbor Press, Cold Spring Harbor, N.Y. (1989), chapters 7, 9, and 11, and in NUCLEIC ACID HYBRIDIZATION, A PRACTICAL APPROACH, Haymes et al., IRL Press, Washington, D.C., 1985.

One non-limiting example of stringent hybridization conditions includes hybridization in 4× sodium chloride/sodium citrate (SSC), at about 65-70° C. (or alternatively hybridization in 4×SSC plus 50% formamide at about 42-50° C.) followed by one or more washes in 1×SSC, at about 65-70° C. A non-limiting example of highly stringent hybridization conditions includes hybridization in 1×SSC, at about 65-70° C. (or alternatively hybridization in 1×SSC plus 50% formamide at about 42-50° C.) followed by one or more washes in 0.3×SSC, at about 65-70° C. A non-limiting example of reduced stringency hybridization conditions includes hybridization in 4×SSC, at about 50-60° C. (or alternatively hybridization in 6×SSC plus 50% formamide at about 40-45° C.) followed by one or more washes in 2×SSC, at about 50-60° C. Stringency conditions with ranges intermediate to the above-recited values, e.g., at 65-70° C. or at 42-50° C. are also intended to be encompassed by the present invention. SSPE (1×SSPE is 0.15M NaCl, 10 mM $NaH_2PO_4$, and 1.25 mM EDTA, pH 7.4) can be substituted for SSC (1×SSC is 0.15M NaCl and 15 mM sodium citrate) in the hybridization and wash buffers; washes are performed for 15 minutes each after hybridization is complete.

The hybridization temperature for hybrids anticipated to be less than 50 base pairs in length should be 5-10° C. less than the melting temperature ($T_m$) of the hybrid, where Tm is determined according to the following equations. For hybrids less than 18 base pairs in length, $T_m$ (° C.)=2(#of A+T bases)+4(#of G+C bases). For hybrids between 18 and 49 base pairs in length, $T_m$ (° C.)=81.5+16.6($\log_{10}$ [Na+])+ 0.41(% G+C)−(600/N), where N is the number of bases in the hybrid, and [Na+] is the concentration of sodium ions in the hybridization buffer ([Na+] for 1×SSC=0.165 M).

The oligonucleotides in kits of the invention may be comprised of any phosphorylation state of ribonucleotides, deoxyribonucleotides, and acyclic nucleotide derivatives, and other functionally equivalent derivatives. Alternatively, the oligonucleotides may have a phosphate-free backbone, which may be comprised of linkages such as carboxymethyl, acetamidate, carbamate, polyamide (peptide nucleic acid (PNA)) and the like (Varma, in MOLECULAR BIOLOGY AND BIOTECHNOLOGY, A COMPREHENSIVE DESK REFERENCE, Meyers, ed., pp. 6 17-20, VCH Publishers, Inc., 1995). The oligonucleotides may be prepared by chemical synthesis using any suitable methodology known in the art, or may be derived from a biological sample, for example, by restriction digestion. The oligonucleotides may contain a detectable label, according to any technique known in the art, including use of radiolabels, fluorescent labels, enzymatic labels, proteins, haptens, antibodies, sequence tags and the like. The oligonucleotides in the kit may be manufactured and marketed as analyte specific reagents (ASRs) or may constitute components of an approved diagnostic device.

In some embodiments, the set of oligonucleotides in the kit have different labels to allow simultaneous determination of the identity of the alleles at two or more polymorphic sites. The oligonucleotides may also comprise an ordered array of oligonucleotides immobilized on a solid surface such as a microchip, silica beads (such as BeadArray technology from Illumina, San Diego, Calif.), or a glass slide (see, e.g., WO 98/20020 and WO 98/20019). Kits comprising such immobilized oligonucleotides may be designed to perform a variety of polymorphism detection assays, including but not limited to probe hybridization and polymerase extension assays.

Kits of the invention may also contain other reagents such as hybridization buffer (e.g., where the oligonucleotides are to be used as allele-specific probes) or dideoxynucleotide triphosphates (ddNTPs; e.g., where the alleles at the polymorphic sites are to be detected by primer extension). Kits designed for use in polymerase-mediated genotyping assays, may also contain a polymerase and a reaction buffer optimized for the polymerase-mediated assay to be performed.

Kits of the invention may also include reagents to detect when a specific hybridization has occurred or a specific polymerase-mediated extension has occurred. Such detection reagents may include biotin- or fluorescent-tagged oligonucleotides or ddNTPs and/or an enzyme-labeled antibody and one or more substrates that generate a detectable signal when acted on by the enzyme.

It will be understood by the skilled artisan that the set of oligonucleotides and reagents for performing the assay will be provided in separate receptacles placed in the kit container if appropriate to preserve biological or chemical activity and enable proper use in the assay.

In other embodiments, each of the oligonucleotides and all other reagents in the kit have been quality tested for optimal performance in an assay designed to determine the genotype for at least one or more of the PS in Table 1 above, e.g., for the rs12748961 SNP. In some embodiments, the kit includes an instruction manual that describes how to use the determined genotype to assign, to the tested nucleic acid sample, the presence or absence of a response marker.

In some preferred embodiments, the set of oligonucleotides in the kit are allele-specific oligonucleotides. As used herein, the term allele-specific oligonucleotide (ASO) means an oligonucleotide that is able, under sufficiently stringent conditions, to hybridize specifically to one allele of a PS, at a target region containing the PS while not hybridizing to the same region containing a different allele. As understood by the skilled artisan, allele-specificity will depend upon a variety of readily optimized stringency conditions, including salt and formamide concentrations, as well as temperatures for both the hybridization and washing steps.

Examples of hybridization and washing conditions typically used for ASO probes and primers are found in Kogan et al., "Genetic Prediction of Hemophilia A" in PCR PROTOCOLS, A GUIDE TO METHODS AND APPLICATIONS, Academic Press, 1990, and Ruaflo et al., *Proc. Natl. Acad. Sci. USA* 87:6296-300 (1990).

Typically, an ASO will be perfectly complementary to one allele while containing a single mismatch for the other allele. In ASO probes, the single mismatch is preferably within a central position of the oligonucleotide probe as it aligns with the polymorphic site in the target region (e.g., approximately the 7th or 8th position in a 15mer, the 8th or 9th position in a 16mer, and the 10th or 11th position in a 20mer). The single mismatch in ASO primers is located at the 3' terminal nucleotide, or preferably at the 3' penultimate nucleotide. ASO probes and primers hybridizing to either the coding or noncoding strand are contemplated by the invention.

In some embodiments, the kit comprises a pair of allele-specific oligonucleotides for each PS to be assayed, with one member of the pair being specific for one allele (e.g., the better response allele) and the other member being specific for the other allele. In such embodiments, the oligonucleotides in the pair may have different lengths or have different detectable labels to allow the user of the kit to determine the genotype for the assayed PS.

In still other preferred embodiments, the oligonucleotides in the kit are primer-extension oligonucleotides. Termination mixes for polymerase-mediated extension from any of these oligonucleotides are chosen to terminate extension of the oligonucleotide at the PS of interest, or one base thereafter, depending on the alternative nucleotides present at the PS.

In another embodiment, the kit comprises a pair of allele specific oligonucleotide probes for genotyping at least one of the polymorphic sites in Table 1. In one embodiment, one ASO probe in the pair comprises a nucleotide sequence of at least 15 nucleotides that is identical to or perfectly complementary to the better response allele of the context sequence shown in Table 2 and the other ASO probe in the pair comprises a nucleotide sequence of at least 15 nucleotides that is identical to or perfectly complementary to the other allele of the context sequence shown in Table 2.

In another embodiment, the kit comprises a pair of allele specific oligonucleotide probes for genotyping the rs12748961 SNP. In one embodiment, one ASO probe in the pair comprises a nucleotide sequence of at least 15 nucleotides that is identical to or perfectly complementary to the better response allele of the rs12748961 SNP and the other ASO probe in the pair comprises a nucleotide sequence of at least 15 nucleotides that is identical to or perfectly complementary to the other allele of the the rs12748961 SNP.

In another embodiment, the kit comprises a pair of allele specific oligonucleotide probes for genotyping the rs12118655 SNP. In one embodiment, one ASO probe in the pair comprises a nucleotide sequence of at least 15 nucleotides that is identical to or perfectly complementary to the better response allele of the rs12118655 SNP and the other ASO probe in the pair comprises a nucleotide sequence of at least 15 nucleotides that is identical to or perfectly complementary to the other allele of the the rs12118655 SNP.

In another embodiment, the kit comprises a pair of allele specific oligonucleotide probes for genotyping the rs6679073 SNP. In one embodiment, one ASO probe in the pair comprises a nucleotide sequence of at least 15 nucleotides that is identical to or perfectly complementary to the better response allele of the rs6679073 SNP and the other ASO probe in the pair comprises a nucleotide sequence of at least 15 nucleotides that is identical to or perfectly complementary to the other allele of the the rs6679073 SNP.

In another embodiment, the kit comprises a pair of allele specific oligonucleotide probes for genotyping the rs12564209 SNP. In one embodiment, one ASO probe in the pair comprises a nucleotide sequence of at least 15 nucleotides that is identical to or perfectly complementary to the better response allele of the rs12564209 SNP and the other ASO probe in the pair comprises a nucleotide sequence of at least 15 nucleotides that is identical to or perfectly complementary to the other allele of the the rs12564209 SNP.

In another embodiment, the kit comprises a pair of allele specific oligonucleotide probes for genotyping the rs3805 SNP. In one embodiment, one ASO probe in the pair comprises a nucleotide sequence of at least 15 nucleotides that is identical to or perfectly complementary to the better response allele of the rs3805 SNP and the other ASO probe in the pair comprises a nucleotide sequence of at least 15 nucleotides that is identical to or perfectly complementary to the other allele of the the rs3805 SNP.

In another embodiment, the kit comprises a pair of allele specific oligonucleotide probes for genotyping the rs71633561 SNP. In one embodiment, one ASO probe in the pair comprises a nucleotide sequence of at least 15 nucleotides that is identical to or perfectly complementary to the better response allele of the rs71633561 SNP and the other ASO probe in the pair comprises a nucleotide sequence of at least 15 nucleotides that is identical to or perfectly complementary to the other allele of the the rs71633561 SNP.

In another embodiment, the kit comprises a pair of allele specific oligonucleotide probes for genotyping the rs71970505 SNP. In one embodiment, one ASO probe in the pair comprises a nucleotide sequence of at least 15 nucleotides that is identical to or perfectly complementary to the better response allele of the rs71970505 SNP and the other ASO probe in the pair comprises a nucleotide sequence of at least 15 nucleotides that is identical to or perfectly complementary to the other allele of the the rs71970505 SNP.

In another embodiment, the kit comprises a pair of allele specific oligonucleotide probes for genotyping the rs12132270 SNP. In one embodiment, one ASO probe in the pair comprises a nucleotide sequence of at least 15 nucleotides that is identical to or perfectly complementary to the better response allele of the rs12132270SNP and the other ASO probe in the pair comprises a nucleotide sequence of at least 15 nucleotides that is identical to or perfectly complementary to the other allele of the the rs12132270 SNP.

In another embodiment, the kit comprises a pair of allele specific oligonucleotide probes for genotyping the rs67625805 SNP. In one embodiment, one ASO probe in the pair comprises a nucleotide sequence of at least 15 nucleotides that is identical to or perfectly complementary to the better response allele of the rs67625805 SNP and the other ASO probe in the pair comprises a nucleotide sequence of at least 15 nucleotides that is identical to or perfectly complementary to the other allele of the the rs67625805 SNP.

In another embodiment, the kit comprises a pair of allele specific oligonucleotide probes for genotyping the rs3747972 SNP. In one embodiment, one ASO probe in the pair comprises a nucleotide sequence of at least 15 nucleotides that is identical to or perfectly complementary to the better response allele of the rs3747972 SNP and the other ASO probe in the pair comprises a nucleotide sequence of at least 15 nucleotides that is identical to or perfectly complementary to the other allele of the the rs3747972 SNP.

In another embodiment, the kit comprises a pair of allele specific oligonucleotide probes for genotyping the rs11557080 SNP. In one embodiment, one ASO probe in the pair comprises a nucleotide sequence of at least 15 nucleotides that is identical to or perfectly complementary to the better response allele of the rs11557080 SNP and the other ASO probe in the pair comprises a nucleotide sequence of at least 15 nucleotides that is identical to or perfectly complementary to the other allele of the the rs11557080 SNP.

In another embodiment, the kit comprises a pair of allele specific oligonucleotide probes for genotyping the rs71633563 SNP. In one embodiment, one ASO probe in the pair comprises a nucleotide sequence of at least 15 nucleotides that is identical to or perfectly complementary to the better response allele of the rs71633563 SNP and the other ASO probe in the pair comprises a nucleotide sequence of at least 15 nucleotides that is identical to or perfectly complementary to the other allele of the the rs71633563 SNP.

In another embodiment, the kit comprises a pair of allele specific oligonucleotide probes for genotyping the rs34848415 SNP. In one embodiment, one ASO probe in the pair comprises a nucleotide sequence of at least 15 nucleotides that is identical to or perfectly complementary to the better response allele of the rs34848415 SNP and the other ASO probe in the pair comprises a nucleotide sequence of at least 15 nucleotides that is identical to or perfectly complementary to the other allele of the the rs34848415 SNP.

In another embodiment, the kit comprises a pair of allele specific oligonucleotide probes for genotyping the rs1891091 SNP. In one embodiment, one ASO probe in the pair comprises a nucleotide sequence of at least 15 nucleotides that is identical to or perfectly complementary to the better response allele of the rs1891091 SNP and the other ASO probe in the pair comprises a nucleotide sequence of at least 15 nucleotides that is identical to or perfectly complementary to the other allele of the the rs1891091 SNP.

B. Pharmaceutical Compositions, Drug Products and Treatment Regimens

An individual to be tested in, or treated by, any of the methods and products described herein is a human subject in need of treatment with a CRTH2 receptor antagonist. In some embodiments, the individual has been diagnosed with, or exhibits a symptom of, a disease susceptible to treatment with a CRTH2 receptor antagonist. In other embodiments, the CRTH2 receptor antagonist drug to be used has been approved for use in treating an indication with which the individual has been diagnosed.

In some embodiments, the CRTH2 receptor antagonist used in the pharmaceutical compositions, drug products, kits methods, and uses of the present invention may be any known CRTH2 receptor antagonist.

In one embodiment, the CRTH2 receptor antagonist is the compound of the formula I as disclosed in U.S. Pat. No. 8,394,819, the disclosure of which is hereby incorporated by reference as if fully set forth herein. This patent discloses a compound of formula I

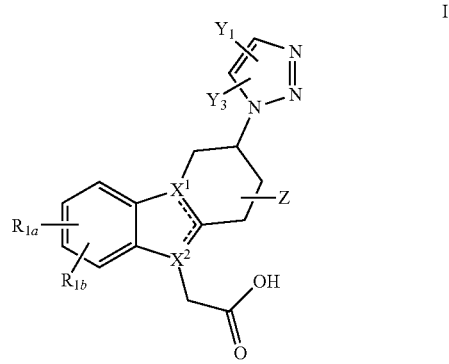

or a pharmaceutically acceptable salt thereof, wherein:

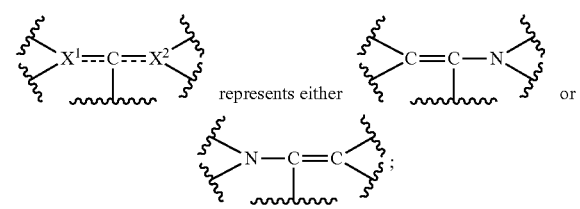

$Y_1$ is selected from optionally substituted aryl and —$C(R_2)(R_3)(R_4)$;
$Y_2$ is selected from H and —$C_{1-6}$alkyl;
Z is selected from H and —$C_{1-6}$alkyl;
$R_{1a}$ and $R_{1b}$ are independently selected from H, halogen, —$OC_{1-6}$alkyl, —O-halo$C_{1-6}$alkyl, —$C_{1-6}$alkyl, halo$C_{1-6}$alkyl, optionally substituted aryl and —($C_{1-3}$alkylene)-optionally substituted aryl;

$R_2$ is selected from H; —$C_{1-6}$alkyl optionally substituted with halogen, —OH or —$NHSO_2CH_3$; —OH; —$OC_{1-6}$alkyl; —$S(O)_nC_{1-6}$alkyl; —CN; optionally substituted aryl; optionally substituted —O-aryl and optionally substituted heteroaryl, wherein n is 0, 1 or 2;

$R_3$ is selected from H, —$C_{1-6}$alkyl, $C_{1-6}$haloalkyl, optionally substituted aryl and optionally substituted heteroaryl; and $R_4$ is selected from H, —$C_{1-6}$alkyl, $C_{1-6}$haloalkyl, optionally substituted aryl and optionally substituted heteroaryl; or $R_3$, $R_4$ and the carbon atom to which they are attached together form —$C_{3-6}$cycloalkyl, fluorenyl or —$C_{3-6}$heterocyclyl having a ring heteroatom selected from —$N(R^a)$—, —O— and —S—; or $R_3$, $R_4$ together represent $C_{1-6}$alkylidene;

$R^a$ is H, $C_{1-6}$alkyl or —$C(O)C_{1-6}$alkyl; and the optional substituent for aryl and heteroaryl is 1 to 4 groups independently selected from halogen, —$C_{1-3}$alkoxy, —$C_{1-3}$haloalkyl, hydroxy-$C_{1-3}$alkyl, —$S(O)n$-$C_{1-3}$alkyl, amino, and mono- and di-($C_{1-3}$alkyl)amino.

In specific embodiments, the CRTH2 receptor antagonist is {(7R)-4-fluoro-7-[5-(4-fluorobenzyl)-1H-[1,2,3]triazol-1-yl]-6,7,8,9-tetrahydropyrido[1,2-a]indol-10-yl}-acetic acid or a pharmaceutically acceptable salt thereof.

In other embodiments, the CRTH2 receptor antagonist is an antagonist disclosed in U.S. Pat. No. 8,592,383, the disclosure of which is hereby incorporated by reference as if fully set forth herein. In specific embodiments, the CRTH2 receptor antagonist is selected from:

4-{cyclopropyl[cis, cis-4-{[4-(trifluoromethoxy)phenyl]carbonyl}-2,3,3a,4,9,9a-hexahydro-1H-cyclopenta[b]quinolin-9-yl]amino}-4-oxobutanoic acid, 4-[cyclopropyl[cis,cis-7-fluoro-2,3,3a,4,9,9a-hexahydro-4-[4-(trifluoromethoxy)benzoyl]-1H-cyclopenta[b]quinolin-9-yl]amino]-4-oxobutanoic acid, 4-(cyclopropyl((3aS,9R,9aR)-7-fluoro-4-(4-(trifluoromethoxy)benzoyl)-2,3,3a,4,9,9a-hexahydro-1H-cyclopenta[b]quinolin-9-yl)amino)-4-oxobutanoic acid, 4-[cyclopropyl[cis,cis-1,2,2a,3,8,8a-hexahydro-3-[4-(trifluoromethoxy)benzoyl]cyclobuta[b]quinolin-8-yl]amino]-4-oxobutanoic acid, (R)-1-((cis,cis-3-(benzyloxycarbonyl)-5,6-difluoro-1,2,2a,3,8,8a-hexahydrocyclobuta[b]quinolin-8-yl)(cyclopropyl)carbamoyl)azetidine-2-carboxylic acid, or a pharmaceutically acceptable salt thereof.

In another embodiment, the compound is 2-(2-methyl-1-(4-(methylsulfonyl)-2-(trifluoromethyl)benzyl)-1H-pyrrolo[2,3-b]pyridin-3-yl)acetic acid (fevipiprant), or a pharmaceutically acceptable salt thereof as disclosed in U.S. Pat. No. 7,666,878.

In another embodiment, the compound is 3-((3R)-3-{[(4-fluorophenyl)sulfonyl]amino}-1,2,3,4-tetrahydro-9H-carbazol-9-yl)propanoic acid (ramatroban) or a pharmaceutically acceptable salt thereof.

In some embodiments, the CRTH2 receptor antagonist is administered in combination with a leukotriene receptor antagonist, such as montelukast, zafilukast, or pranlukast. In specific embodiments, the leukotriene receptor antagonist is montelukast. The CRTH2 receptor antagonist and leukotriene receptor antagonist can be administered in the same or separate dosage forms.

In specific embodiments of the combination therapy, the CRTH2 antagonist is {(7R)-4-fluoro-7-[5-(4-fluorobenzyl)-1H-[1,2,3]triazol-1-yl]-6,7,8,9-tetrahydropyrido[1,2-a]indol-10-yl}-acetic acid or a pharmaceutically acceptable salt thereof, and the leukotriene receptor antagonist is montelukast. In other specific embodiments, the CRTH2 receptor antagonist is fevipiprant or a pharmaceutically acceptable salt thereof and the leukotriene receptor antagonist is montelukast.

Disorders that may be treated with the pharmaceutical compositions, drug products, kits, methods, and uses of the present invention in accordance with the present invention are generally those that are susceptible to treatment with CRTH2 receptor antagonist therapy, i.e., the CRTH2 receptor antagonist achieves a clinically measurable beneficial result in a group of patients with the disease. Exemplary diseases and conditions susceptible to treatment with a CRTH2 receptor antagonist include but are not limited to diseases include asthma, congestion, allergic rhinitis, atopic dermatitis, chronic obstructive pulmonary disease ("COPD"), dermatitis, inflammatory bowel disease, rheumatoid arthritis, allergic nephritis, conjunctivitis, bronchial asthma, food allergy, systemic mast cell disorder, anaphylactic shock, urticaria, eczema, itching, inflammation, ischemia-reperfusion injury, cerebrovascular disorders, pleuritis, ulcerative colitis, eosinophil-related diseases, such as Churg-Strauss syndrome and sinusitis, and basophile-related diseases, such as basophilic leukemia and basophilic leukocytosis, in humans and other mammals. Examples of cerebrovascular disorders include stroke.

In certain embodiments, the present invention provides a pharmaceutical composition, drug product, kit, method, or use for treating asthma, congestion, allergic rhinitis or COPD which include instructions for administering a therapeutically effective dose of CRTH2 receptor antagonist to a patient in need of such treatment. In a specific embodiment, the disease or condition being treated is asthma. In another embodiment, the disease or condition being treated is COPD.

In addition, the $CRTH_2$ receptor antagonists can inhibit prostanoid-induced smooth muscle contraction by antagonizing contractile prostanoids or mimicking relaxing prostanoids and hence may be used in the inventive methods of treatment for dysmenorrhea, premature labor and eosinophil-related disorders.

In preferred embodiments, the CRTH2 receptor antagonist response marker of the present invention is used in conjunction with any CRTH2 receptor antagonist monotherapy or combination therapy treatment regimen comprising a CRTH2 receptor antagonist and a leukotriene receptor antagonist, e.g., montelukast, for treating asthma, including allergic asthma.

The doses and dosage regimen of the other agents used in the combination therapies of the present invention for the treatment of disorders susceptible to treatment by a CRTH2 antagonist can be determined by the attending clinician, taking into consideration the approved doses and dosage regimen in the package insert; and the age, sex and general health of the patient. Agents administered in combination therapy can be administered simultaneously (i.e., in the same composition or in separate compositions one right after the other) or sequentially. This is particularly useful when the components of the combination are given on different dosing schedules, e.g., one component is administered once daily and another every six hours, or when the preferred pharmaceutical compositions are different, e.g., one is a tablet and one is a capsule. A kit comprising the separate dosage forms is therefore advantageous.

When administering a combination therapy that is selected to treat a patient based on the presence or absence of a CRTH2 receptor antagonist response marker in the patient, the therapeutic agents in the combination, or a pharmaceutical composition or compositions comprising the therapeutic agents, may be administered in any order such as, for example, sequentially, concurrently, together, simultaneously and the like. The amounts of the various therapeutic agents in such combination therapy may be different amounts (different dosage amounts) or same amounts (same dosage amounts). In some embodiments, the agents in the combination are administered in doses commonly employed when such agents are used as monotherapy for treating the patient's disease or condition, while in other embodiments, the agents are administered in doses lower than the doses commonly employed when such agents are used as monotherapy for treating the disease or condition.

In some embodiments, the therapeutic agents used in combination therapy are present in the same pharmaceutical composition, which may be suitable for oral administration, intravenous administration, subcutaneous administration or parenteral administration.

In a specific embodiment, the therapeutic agents used in combination therapy are present in the same pharmaceutical composition, which is a tablet suitable for oral administration.

The inventors herein also contemplate that the CRTH2 receptor antagonist response marker described herein could be used to seek regulatory approval to market a new CRTH2 receptor antagonist drug product for a pharmacogenetic indication, i.e., an indication that includes a disease component and a CRTH2 receptor antagonist marker component. The disease component is a disease susceptible to treatment with the CRTH2 receptor antagonist and the genetic marker component is a patient who tests positive for at least one copy of one of the better response alleles as set forth in Table 1 (e.g., for at least one of one copy of the C allele of the rs12748961 SNP. Similarly, the inventors herein contemplate that the CRTH2 receptor antagonist response marker is useful for seeking approval of such pharmacogenetic indications for currently approved CRTH2 receptor antagonist drugs that physicians are reluctant to prescribe for certain diseases based on the marginal benefit/risk ratio of the drug for such diseases in the general population.

Seeking approval for a pharmacogenetic indication typically involves measuring the incidence of a desired response to a drug in two separate groups of patients treated with the drug. Each individual within one of the groups has disease and genetic profiles that place the individual within the proposed pharmacogenetic indication. The individuals in the other group may be randomly selected without regard to whether they have the genetic marker component of the proposed pharmacogenetic indication. Alternately, the individuals are assigned to the other group in a manner that results in a "control" group in which the percentage of individuals who meet and do not meet the genetic marker component is similar to what is observed in the general population, or in a population of patients with the disease component of the proposed pharmacogenetic indication. The drug product for which approval is sought could be administered to the two groups in a prospective trial. Alternatively, a retrospective pharmacogenetic analysis of patients previously treated with the drug could be performed.

The drug product for which a pharmacogenetic indication is being sought could be evaluated with other therapeutically active agents, for example another drug with efficacy for treating the disease or condition in the proposed pharmacogenetic indication or an agent that is intended to reduce the incidence of an adverse effect caused by the drug. In some embodiments, the pharmacogenetic indication for which regulatory approval is sought may include other markers (genetic markers or biomarkers) or predictors of response to the drug.

The pharmacogenetic study could be designed in consultation with representatives of the regulatory agency or government entity from whom approval is required before marketing the pharmacogenetic drug product in a particular country. Preferably, the regulatory agency is authorized by the government of a major industrialized country, such as Australia, Canada, China, a member of the European Union, Japan, South Korea, Taiwan and the like. Most preferably the regulatory agency is authorized by the government of the United States and the type of application for approval that is filed will depend on the legal requirements set forth in the last enacted version of the Food, Drug and Cosmetic Act that are applicable for the drug product and may also include other considerations such as the cost of making the regulatory filing and the marketing strategy for the drug product. For example, if the pharmaceutical formulation in the drug product has previously been approved for the disease component of the proposed pharmacogenetic indication, then the application might be a paper NDA, a supplemental NDA or an abbreviated NDA, but the application might need to be a full NDA if the pharmaceutical formulation has never been approved before; with these terms having the meanings applied to them by those skilled in the pharmaceutical arts or as defined in the Drug Price Competition and Patent Term Restoration Act of 1984.

One desired outcome of a pharmacogenetic clinical trial using the CRTH2 receptor response marker of the invention is approval to market a drug product which comprises (1) a CRTH2 receptor antagonist pharmaceutical composition and (2) prescribing information which includes a pharmacogenetic indication for which the pharmaceutical composition is recommended. Prescribing information is typically found in the product insert, also frequently referred to as the package insert or label, for the drug.

As discussed above, the pharmacogenetic indication has two components: a disease component and the CRTH2 receptor response marker component. Thus, the prescribing information would describe a genetically defined group of patients for which the drug has demonstrated efficacy for one or more diseases, symptoms or medical conditions. In some embodiments, the prescribing information will discuss how to identify individuals who are in the genetically defined group. For example, in some embodiments, the prescribing information states that the drug is indicated for individuals who test positive for the better response allele of a CRTH2 receptor antagonist response marker described herein. Alternately, the prescribing information may state that the drug is contraindicated for individuals who test negative for a better response allele of a CRTH2 receptor antagonist response marker described herein. In some preferred embodiments, the prescribing information includes the name of at least one approved diagnostic test to be used for detecting the presence or absence of the required genetic marker component of the pharmacogenetic indication. As described above, a pharmacogenetic indication in a pharmacogenetic drug product of the invention may include additional markers or predictors of response to the CRTH2 receptor antagonist pharmaceutical composition and/or a requirement to use the drug in combination with one or more other therapeutically active agents (e.g., montelukast). The prescribing information may include information on recommended dosages and treatment regimens.

In preferred pharmacogenetic drug products of the invention, the pharmaceutical composition comprises a CRTH2 receptor antagonist selected from {(7R)-4-fluoro-7-[5-(4-fluorobenzyl)-1H-[1,2,3]triazol-1-yl]-6,7,8,9-tetrahydropyrido[1,2-a]indol-10-yl}-acetic acid and fevipiprant. More preferably, the pharmaceutical composition comprises a CRTH2 receptor antagonist which is {(7R)-4-fluoro-7-[5-(4-fluorobenzyl)-1H-[1,2,3]triazol-1-yl]-6,7,8,9-tetrahydropyrido[1,2-a]indol-10-yl}-acetic acid and a leukotriene receptor antagonist such as montelukast. A preferred pharmacogenetic indication for the drug products of the invention comprises the use of the pharmaceutical composition for the treatment of patients suffering from asthma and at least one copy of one of the better response alleles for the CRTH2 response antagonist markers set forth in Table 1. In preferred embodiments, the patients test positive for at least one copy of the C allele for the rs12748961 SNP. In some embodiments, the prescribing information states that the CRTH2 receptor antagonist pharmaceutical composition is indicated in combination with a leukotriene receptor antagonist (e.g., montelukast) for treating patients suffering from asthma.

Any or all analytical and mathematical operations involved in performing the methods and uses described herein or in using the kits, composition and drug products described herein may be implemented by a computer. For example, the computer may execute a computer program that assigns the presence or absence of the better response allele of the CRTH2 receptor antagonist response marker to an individual based on genotype data inputted by an employee of a testing laboratory or by the treating physician. In addition, the same computer or a different computer may output the predicted response to CRTH2 receptor antagonist therapy based on that response marker assignment. Data relating to the presence or absence of the better response allele of a CRTH2 receptor antagonist response marker in an individual may be stored as part of a relational database (e.g., an instance of an Oracle database or a set of ASCII flat files) containing other clinical and/or genetic data for the individual. These data may be stored on the computer's hard drive or may, for example, be stored on a CD ROM or on one or more other storage devices accessible by the computer. For example, the data may be stored on one or more databases in communication with the computer via a network.

EXAMPLES

The following examples are provided to more clearly describe the present invention and should not be construed to limit the scope of the invention.

Example 1. Identification of the Single Nucleotide Polymorphism (SNP) Associated with $FEV_1$ Response to Treatment with CRTH2 Receptor Antagonist/Montelukast Combination Therapy In order to identify genetic contributions to treatment response, the inventors conducted a pharmacogenetic (PGx) analysis on asthmatic study subjects who had undergone a clinical trial with a CRTH2 receptor antagonist to assess whether the mean treatment difference varies across patient subgroups defined by several pre-specified single nucleotide polymorphisms (SNPs).

Summary of the Clinical Study Design

FIG. 2 is graphical depiction of the study design. The study was a 17-week randomized, double-blind, placebo-controlled, crossover study with in-house blinding to evaluate the effect of {(7R)-4-fluoro-7-[5-(4-fluorobenzyl)-1H-[1,2,3]triazol-1-yl]-6,7,8,9-tetrahydropyrido[1,2-a]indol-10-yl}-acetic acid (hereinafter "Compound A") on $FEV_1$ when dosed for 4 weeks in asthmatic subjects with persistent symptoms while receiving montelukast (ML). Overall, 104 patients completed the study. Period I was a pre-study period. Subjects receiving long acting beta-agonists (LABAs) with inhaled corticosteroid (ICS), either separately or as part of a fixed-dose combination, were asked to discontinue the LABA component while still receiving ICS. Period II was a 2- to 4-week run-in period during which subjects receive open-label montelukast (ML) and single-blind placebo (PBO). Subjects receiving ICS or other controllers were required to taper off these medications while receiving montelukast; Period III was a 4-week, double-blind, randomized treatment period during which subjects received either Compound A 150 mg or matching-image placebo while continuing to receive montelukast 10 mg QD; Period IV was a 4-week wash out period during which subjects receive placebo in a single-blind fashion while continuing to receive montelukast 10 mg QD; Period V was a 4-week double-blind period during which subjects were crossed over to the opposite treatment not received during Period III.

The primary efficacy endpoint of the study was forced expiratory volume in 1 second ($FEV_1$) after 4 weeks of dosing, and the study had 85% power to detect a true overall mean treatment difference of 110 mL.

A pharmacogenetic analysis was also performed to assess whether the mean treatment difference varies across patient subgroups defined by several pre-specified SNPs.

Genotype and Clinical Data

Based on a pre-specified list of single nucleotide polymorphisms (SNPs) associated with the CRTH2 gene, peripheral blood eosinophil and basophil counts, serum IgE levels and periostin lung expression quantitive trait loci (eQTLs), genetic data for 5,092 SNPs were generated using a next generation sequencing platform. After removal of SNPs with no observed genotype variation, 85 remained. Subsequent dropping of SNPs with minor allele frequency (MAF) <1% resulted in 70 SNPs being included in the pharmacogenetics statistical analysis.

The efficacy data set for the pharmacogenetics analysis was based on 103 patients since one of the study subjects who completed the study was excluded because no genotyping data was collected for this patient.

Statistical Methods

Evaluation of the Overall Mean Treatment Difference in $FEV_1$ (Ignoring Genetics)

A common analysis for crossover designs with longitudinal measurements in each period uses a linear mixed effects "cell means" model with the clinical measure (here, $FEV_1$) as the dependent variable, and sequence (S=M→P, P→M), treatment (T=M,P), visit (V=0, 2, 4 weeks), and all possible interactions involving S, T, and V as independent variables; M=Compound A+montelukast, P=placebo+montelukast. In addition, to minimize assumptions, a covariance matrix without imposition of any structure (such as compound symmetry) is used to account for the intra-patient correlations among $FEV_1$ responses over time and across the two treatments within each sequence.

This common analysis can be misleading if both of the following conditions are encountered in either crossover sequence: (i) the observed mean difference in baseline means for the two treatments is "far" from zero, and (ii) baseline and post-baseline responses are very strongly correlated (correlation 0.9 or higher). In preparation for the pharmacogenetic analysis, both of these conditions were observed in the $FEV_1$ data. Consequently, we analyzed the FEV$_1$ data using an extension of the method of analysis described in Mehrotra D V, *Pharmaceutical Statistics* 13, 376-387 (2014). This second analytical method is specifically designed for crossover analyses with baseline measurements. To do so, we added "xdiff" (baseline difference between treatments M and P) and interactions between xdiff and all the other fixed effect terms involving S, T, and V to the aforementioned common analysis crossover model; the mean treatment difference at week 4 was estimated at xdiff=0 via the SAS code below.

```
PROC MIXED DATA=pgxsub;
    WHERE visit>0;
    CLASS seq trt visit subjid;
    MODEL fev1=seq|trt|visit|xdiff/DDFM=KR;
    REPEATED trt*visit/SUBJECT=subjid TYPE=UN;
    LSMEANS trt*visit/AT xdiff=0 PDIFF CL;
RUN;
```

In the SAS code above, patients with a missing xdiff value are automatically removed from the analysis. To generate results in which all 103 patients are retained in the analysis, missing period 2 baseline FEV$_1$ values (resulting in missing xdiff values, which was the case for ~20% of the patients due to dropout) were imputed separately in each sequence via a simple linear regression model with the period 2 baseline as the dependent variable and the corresponding period 1 baseline as the independent variable. As noted earlier, the observed correlation between period 1 and period 2 FEV$_1$ baselines was 0.9 in both sequences, providing reassurance that the imputed values for missing period 2 baselines had good reliability.

The key difference between the standard crossover analysis and the second analysis described above can be explained via their respective estimands (i.e., target parameters). The estimand for the former is $E[(Y_M-X_M)-(Y_P-X_P)]=E[(Y_M-Y_P)-(X_M-X_P)]$, where $E(z)$ denotes the population mean of z, while the estimand for the latter is $E[(Y_M-Y_P)|(X_M-X_P)=0]$, where $X_M$ is the baseline FEV$_1$ before treatment M, $Y_M$ is the week 4 FEV$_1$ following treatment M, and so on. Note that the new analysis "adjusts" for a baseline imbalance when comparing post-baseline FEV$_1$ values between treatments by imposing the condition $X_M-X_P=0$ (or equivalently, $X_M=X_P$); this conditioning ensures a fair comparison of M and P while also reducing the variability of the estimate of the target parameter, relative to the standard analysis.

PGx Analysis: Assessing Whether Mean Treatment Differences in FEV$_1$ are Associated with SNP(s)

For the pharmacogenetics analysis, in the model just described above, fixed effect terms for genotype (coded as G=0, 1, or 2 depending on the number of minor alleles for the given SNP) and treatment by genotype interaction were added, the latter being of primary interest. To avoid instability in estimated model parameters, for any given SNP, the G=1 and G=2 genetic subgroups were combined if the number of patients in the latter subgroup was less than 5. Each SNP was analyzed separately. The following SAS code was used for the PGx analysis:

```
PROC MIXED DATA=pgxsub;
    WHERE visit>0;
    CLASS seq trt visit subjid;
    MODEL fev1=seq|trt|visit|xdiff g trt*g/DDFM=KR;
    REPEATED trt*visit/SUBJECT=subjid TYPE=UN;
    ESTIMATE 'TxG interaction' trt*g 1 -1/CL;
    LSMEANS trt*visit/AT (xdiff g)=(0 0) PDIFF CL;
    LSMEANS trt*visit/AT (xdiff g)=(0 1) PDIFF CL;
    LSMEANS trt*visit/AT (xdiff g)=(0 2) PDIFF CL;
    ODS OUTPUT ESTIMATES=pgxout;
    BY SNP;
RUN;
```

The 70 p-values (one for each SNP) derived via the above SAS code were evaluated for statistical significance after a Bonferroni adjustment. Accordingly, a SNP was deemed statistically significant if the associated p-value was less than 0.05/70=0.00071

Sensitivity analyses: To assess robustness of the main pharmacogenetic analysis described above, sensitivity analyses were conducted in which terms for race-group and treatment by race-group interaction were included in the pharmacogenetics analysis model, with race-group represented as a binary indicator variable for self-reported race of either "white"/other or "multiple"/other.

Results

Evaluation of the Overall Mean Treatment Difference at Week 4 (Ignoring Genetics)

Table 3 displays FEV$_1$ (mL) summary statistics by sequence and treatment for week 0 (baseline), week 4, and change from baseline at week 4. The last two columns show summary statistics for derived within-patient variables Xdiff (difference in baseline values prior to M and P) and ΔΔ (difference in change from baseline after M and P), both based on completers only.

Two observations in Table 3 are noteworthy. First, while the baseline means prior to administration of M and P are similar in the M→P sequence (2270 vs. 2297 mL), they are notably different in the P→M sequence (2452 vs. 2226 mL) based on all patients with available data; the same concern about a baseline imbalance in the P→M sequence surfaces when focusing on the completers only based on the Xdiff mean of 153 mL. Second, the mean ΔΔ values are also strikingly different between the two sequences; the mean ΔΔ of 133 mL in the first sequence is larger than the 110 mL effect that the trial was designed to detect, but the corresponding observed difference in the second sequence is in the opposite direction (−78 mL).

TABLE 3

FEV$_1$ (mL) summaries for observed data and relevant derived variables

| | | Compound A + montelukast [M] | | | Placebo + montelukast [P] | | | Completers only | |
|---|---|---|---|---|---|---|---|---|---|
| | | W 0 | W 4 | W 4 − W 0 | W 0 | W 4 | W 4 − W 0 | Xdiff | ΔΔ |
| M→P | Mean | 2270 | 2365 | 96 | 2297 | 2258 | −23 | −24 | 133 |
| (N = 51) | (SE) | (78) | (95) | (49) | (97) | (98) | (46) | (47) | (65) |
| | N | 57 | 46 | 46 | 44 | 39 | 39 | 38 | 38 |

TABLE 3-continued

FEV$_1$ (mL) summaries for observed data and relevant derived variables

| | | Compound A + montelukast [M] | | | Placebo + montelukast [P] | | | Completers only | |
|---|---|---|---|---|---|---|---|---|---|
| | | W 0 | W 4 | W 4 − W 0 | W 0 | W 4 | W 4 − W 0 | Xdiff | ΔΔ |
| P→M | Mean | 2452 | 2507 | 42 | 2226 | 2290 | 58 | 153 | −78 |
| (N = 52) | (SE) | (96) | (97) | (42) | (82) | (100) | (41) | (41) | (66) |
| | N | 41 | 39 | 39 | 52 | 48 | 48 | 39 | 39 |

SE = standard error;
ΔΔ = treatment difference [M − P] in change from baseline at week 4 (W 4 − W 0)

Results based on the second analytical method described in the Statistical Methods section, where xdiff is used as a covariate and estimation of the mean treatment difference is obtained after imposing the condition xdiff=0, are given in Table 4.

TABLE 4

Estimated mean treatment difference in FEV$_1$ (mL) at Week 4 using the new method of analysis

| | Missing period 2 FEV$_1$ baselines imputed:* | |
|---|---|---|
| | No (N = 85**) | Yes (N = 103) |
| LSMean | 120 | 122 |
| (95% CI) | (56,184) | (56,187) |
| P-value | .0004 | .0004 |

*regression-based imputation of period 2 baseline given period 1 baseline in the given sequence;
**N is the number of patients included in the analysis.

The results in Table 4 suggest that, relative to placebo, Compound A appears to be notably more effective in improving FEV$_1$ levels, on average, after four weeks of treatment in patients who continue to take montelukast as background therapy.

The pharmacogenetic analysis results described below inform on whether the apparent mean net benefit of ~120 mL is evenly distributed across the trial population or driven primarily by a genetics-based subgroup.

PGx Analysis: Assessing Whether Mean Treatment Differences in FEV$_1$ are Associated with SNP(s)

A total of 70 SNPs were assessed in the analysis. Among the 70 SNPs analyzed, only one (rs12748961) had a p-value that was smaller than the Bonferroni threshold of 0.00071.

Table 5 shows the estimated mean treatment difference at week 4 by genotype subgroup for SNP rs12748961, along with the statistically significant p-value for the treatment by genotype interaction. For this SNP, the number of patients in the C=0, 1 and 2 genetic subgroups were 74, 27 and 2, respectively; the latter two subgroups were combined prior to the PGx analysis, for reasons noted in the Statistical Methods section.

TABLE 5

FEV$_1$ (mL): Estimated Mean Treatment Difference at Week 4 by Genotype Subgroup for rs12748961

| | C = 0 (N = 74) | C ≥ 1 (N = 29) | Test for Treatment by Genotype interaction |
|---|---|---|---|
| LSMean | 59 | 268 | p = 0.0005* |
| (95% CI) | (−11,129) | (167,370) | |

*less than the Bonferroni-adjusted p-value threshold of .05/70 = .00071 to account for 70 statistical tests.
C is number of copies of the C allele.

Figure 3:
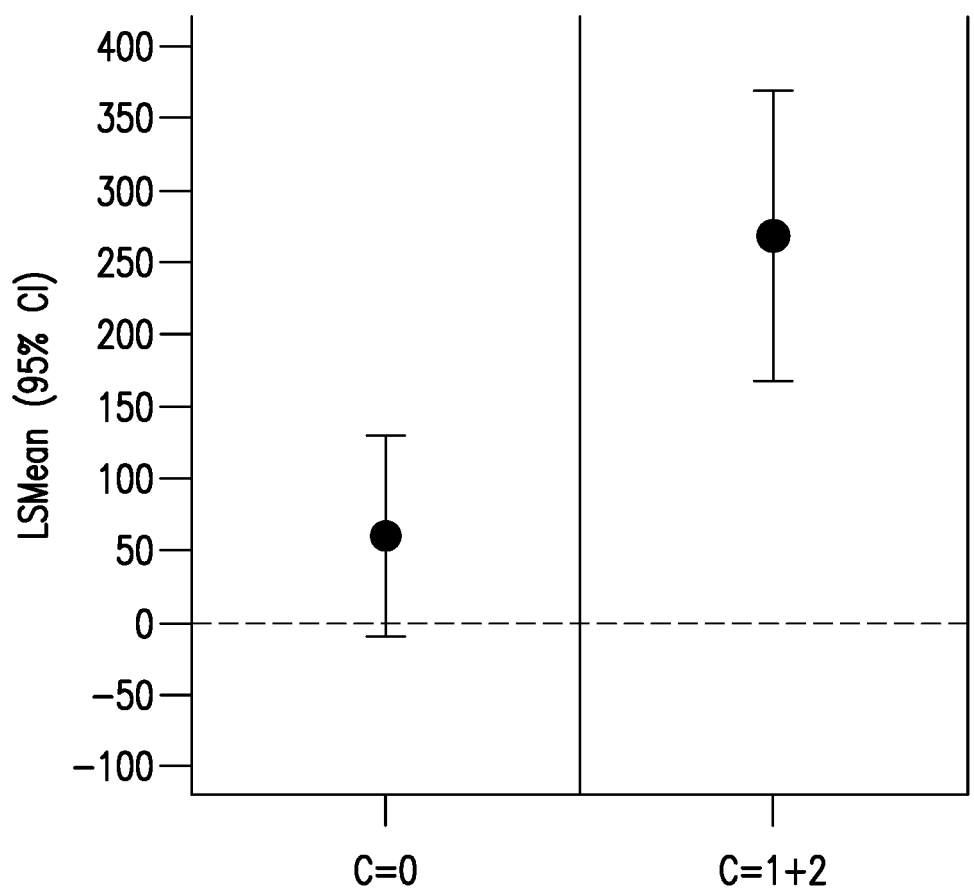
FIG. 3 illustrates the estimated mean within-patient difference in $FEV_1$ score improvement (mL) at Week 4 between a combination of Compound A and montelukast vs. a combination of placebo and montelukast in individuals who carry no copies of the C allele (C=0) and in individuals who carry one or two copies of the C allele (C=1+2) at rs12748961 from the clinical study summarized in FIG. 2.

A graphical representation of the results in Table 5 is provided in FIG. 3. The apparently beneficial overall drug effect appears to be largely driven by the mean of ~30% of the trial population who possess at least one copy of the C allele (C≥1) of the rs12748961 SNP; the estimated benefit of Compound A in the remaining 70% of the patients appears to be relatively small.

Sensitivity analyses in which terms for race-group and treatment by race-group interaction were added to the pharmacogenetics analysis model delivered results that were very similar to those reported above for all the SNPs.

Figure 4:
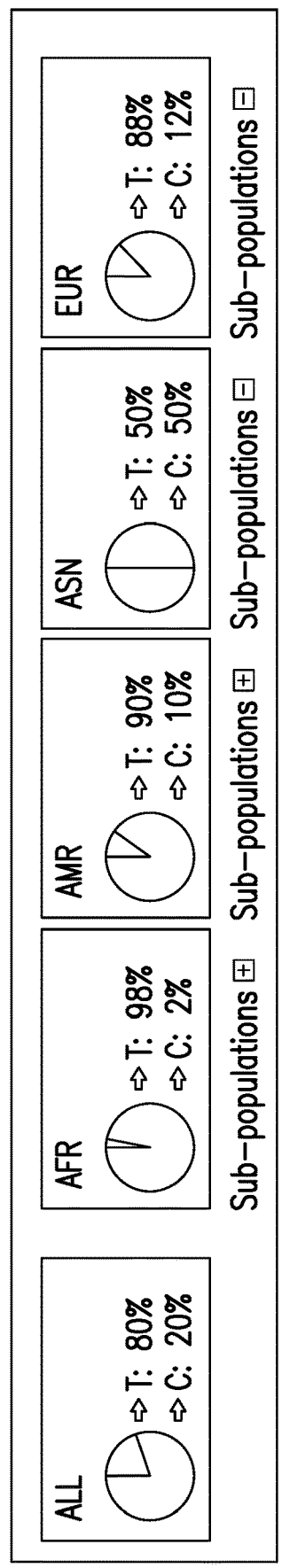
FIG. 4 shows the the minor allele (C) frequency for rs12749861 overall and across different populations based on the 1000 Genomes data set.

The minor allele frequency for rs12748961 is reported to be ~20%, as established by the 1000 Genomes Project, based on the world-wide population, as shown in FIG. 4. Paul Julian Kersey et al., "Ensembl Genomes 2013: scaling up access to genome-wide data," *Nucleic Acids Research* 2014, 42 (D1): D546-D552. However, there are dramatic differences in its frequency between the Asian versus African populations as is also shown in FIG. 4, which might provide unique medical and/or commercial opportunities in treating populations having a higher frequency of the C allele with CRTH2 receptor antagonists, such as Compound A.

Example 2. Identification of Additional Genetic Variants Associated with FEV$_1$ Response to Treatment with CRTH2 Receptor Antagonist/Montelukast Combination Therapy A second investigation was performed to identify additional genetic markers other than rs12748961, that are predictive of a beneficial response to CRTH2 receptor antagonist/montelukast combination.

Blood samples from patients from the study described above were further genotyped using the Merck Custom Axiom Array. The Merck Custom Axiom Array was designed using the UK Biobank Axiom Genotyping Array as a backbone with custom content to include more diversity for common SNPs in different ethnic populations and additional content for drug metabolizing enzymes. This investigation comprised the same patient population as described above in Example 1, except that one patient's data was excluded because too little DNA was available for further genotyping. Data from a total of 102 subjects were included in this investigation.

Genetic imputation was performed based on the assayed variants on Merck Custom Axiom Array (after genetic quality control) using the IMPUTE2 software which is an genotype imputation and haplotype phasing program based on the disclosure in B. N. Howie, et al., "A flexible and accurate genotype imputation method for the next generation of genome-wide association studies," *PLoS Genetics* (2009) 5(6): e1000529. As explained in Howie et al., imputation methods predict unobserved genotypes in a study sample by using a population genetic model to extrapolate allelic correlations measured in a reference panel. In this case, sequence data from the 1000 Genome Project were used as the imputation reference dataset. Imputed variants with low imputation certainty (information metric <0.3) were excluded from the analysis.

This investigation comprised testing all PSs with a minor allele frequency (MAF) >0.05 in the region of 200 kB with rs12748961, for both assayed and imputed PSs. A total of 1054 PSs (including 111 assayed variants) were analyzed. The same statistical method as described in Example 1 was applied in this analysis.

Table 6 lists the PSs which show or are predicted to have a treatment effect by genotype interaction with a p-value of <0.001. The minor allele frequency (MAF) based on the analysis dataset is reported in the second column. The third column indicates whether the particular PS was assayed via the Axiom Merck Custom Array. The fifth column indicates the Pearson correlation squared with respect to presence of the C allele of the rs12748961 SNP.

TABLE 6

| PS | MAF | Assayed | p-value | r2 with rs12748961 |
|---|---|---|---|---|
| rs12748961 | 0.152 | Y | 0.00054 | 1.00 |
| rs12118655 | 0.152 | Y | 0.00010 | 0.93 |

TABLE 6-continued

| PS | MAF | Assayed | p-value | r2 with rs12748961 |
|---|---|---|---|---|
| rs6679073 | 0.223 | | 0.00048 | 0.52 |
| rs12564209 | 0.152 | | 0.00054 | 1.00 |
| rs3805 | 0.157 | | 0.00054 | 0.97 |
| rs71633561 | 0.152 | | 0.00054 | 1.00 |
| rs71970505 | 0.152 | | 0.00054 | 1.00 |
| rs12132270 | 0.157 | | 0.00055 | 0.89 |
| rs67625805 | 0.170 | | 0.00076 | 0.91 |
| rs3747972 | 0.162 | | 0.00076 | 0.93 |
| rs11557080 | 0.157 | | 0.00086 | 0.96 |
| rs71633563 | 0.157 | Y | 0.00086 | 0.96 |
| rs34848415 | 0.396 | | 0.00092 | 0.09 |
| rs1891091 | 0.137 | | 0.00113 | 0.89 |

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

Patents, patent applications, publications, product descriptions, and protocols are cited throughout this application, the disclosures of which are incorporated herein by reference in their entireties for all purposes.

We claim:

1. A method of treating a patient with asthma comprising:
    administering a therapeutically effective amount of {(7R)-4-fluoro-7-[5-(4-fluorobenzyl)-1H-[1,2,3]triazol-1-yl]-6,7,8,9-tetrahydropyrido[1,2-a]indol-10-yl}-acetic acid or a pharmaceutically acceptable salt thereof to the patient,
    wherein said patient, prior to the administration of the {(7R)-4-fluoro-7-[5-(4-fluorobenzyl)-1H-[1,2,3]triazol-1-yl]-6,7,8,9-tetrahydropyrido[1,2-a]indol-10-yl}-acetic acid or the pharmaceutically acceptable salt thereof, has tested positive for at least one copy of the C allele of the rs12748961 SNP.

2. A method of diagnosing in a patient who is susceptible to treatment with {(7R)-4-fluoro-7-[5-(4-fluorobenzyl)-1H-[1,2,3]triazol-1-yl]-6,7,8,9-tetrahydropyrido[1,2-a]indol-10-yl}-acetic acid or a pharmaceutically acceptable salt thereof and treating asthma, said method comprising:
    (a) obtaining a biological sample from a human patient;
    (b) detecting whether the C allele of the CRTH2 receptor antagonist response marker is rs12748961 SNP is present in the biological sample;
    (c) diagnosing the patient as susceptible to treatment with {(7R)-4-fluoro-7-[5-(4-fluorobenzyl)-1H-[1,2,3]triazol-1-yl]-6,7,8,9-tetrahydropyrido[1,2-a]indol-10-yl}-acetic acid when the presence of the C allele of the rs12748961 SNP is detected; and
    (d) administering a therapeutically effective amount of {(7R)-4-fluoro-7-[5-(4-fluorobenzyl)-1H-[1,2,3]triazol-1-yl]-6,7,8,9-tetrahydropyrido[1,2-a]indol-10-yl}-acetic acid or a pharmaceutically acceptable salt thereof a to the diagnosed patient.

3. The method of claim 2, wherein step (d) further comprises administering a leukotriene receptor antagonist to the patient.

4. The method of claim 3, wherein in step (d) the leukotriene receptor antagonist is montelukast or a pharmaceutically acceptable salt thereof.

5. The method of claim 1, wherein montelukast is administered to the patient in addition to {(7R)-4-fluoro-7-[5-(4-fluorobenzyl)-1H-[1,2,3]triazol-1-yl]-6,7,8,9-tetrahydropyrido[1,2-a]indol-10-yl}-acetic acid or a pharmaceutically acceptable salt thereof.

* * * * *

SEQUENCE LISTING

```
<160> NUMBER OF SEQ ID NOS: 15

<210> SEQ ID NO 1
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: can be C or T

<400> SEQUENCE: 1
ctcttcacta tgttgaaatt gggtcnttct tccccaaaga ttgaagagaa t          51

<210> SEQ ID NO 2
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: can be A or G

<400> SEQUENCE: 2
tcagatggga aatattgcag gggctntatg gtctccatcg caactactca c          51

<210> SEQ ID NO 3
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: can be A or C

<400> SEQUENCE: 3
ttttgagact ggcaaatgtt ctgcanccag tatctgctca atactttgt g           51

<210> SEQ ID NO 4
```

```
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: can be C or G

<400> SEQUENCE: 4
caaaagtctt taggatagtc tctggntcac agtaagtgct acgtaagtgt t           51

<210> SEQ ID NO 5
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: can be A, G or T

<400> SEQUENCE: 5
tttttataca tgttatttta gggcanaagc tgagtactat accccccacac c          51

<210> SEQ ID NO 6
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: can be C or G

<400> SEQUENCE: 6
gaggtaggag aatcacttga acccangggt cagaggttgt ggtgagccga g           51

<210> SEQ ID NO 7
<211> LENGTH: 61
<212> TYPE: DNA
<213> ORGANISM: Homo sapiens

<400> SEQUENCE: 7
agtttgcaaa gtaacccatt tggccatgca gactgtaagt catacaactc tagagggaca  60
a                                                                  61

<210> SEQ ID NO 8
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: can be C or T

<400> SEQUENCE: 8
ctcctatctc cattttactc ttatgnctac ccccagaata ggttttctgg a           51

<210> SEQ ID NO 9
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: can be absent or T

<400> SEQUENCE: 9
ggtggtaatg tatatttatc ttaaantttt ttttttttt tgagacggag t            51
```

<210> SEQ ID NO 10
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: can be A or G

<400> SEQUENCE: 10
gcggatcgcc tgagatcagg agttcnagac cagcctggcc aacatggtga a          51

<210> SEQ ID NO 11
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: can be A or G

<400> SEQUENCE: 11
cgcaatggtg tgatctcagc tcactncaac ctctaactcc caggttcaag c          51

<210> SEQ ID NO 12
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: can be C or T

<400> SEQUENCE: 12
ctgcctacaa aagtatcagg caaganaggc ctcacgttag atgagatagt a          51

<210> SEQ ID NO 13
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: can be absent or A

<400> SEQUENCE: 13
ggcaataaga gtgaaactcc atctcnaaaa aaaaaaaaa aaaatctatt t           51

<210> SEQ ID NO 14
<211> LENGTH: 50
<212> TYPE: DNA
<213> ORGANISM: Homo sapiens

<400> SEQUENCE: 14
agtttgcaaa gtaacccatt tggccaagtc atacaactct agagggacaa            50

<210> SEQ ID NO 15
<211> LENGTH: 51
<212> TYPE: DNA
<213> ORGANISM: Homo sapiens
<220> FEATURE:
<221> NAME/KEY: misc_feature
<222> LOCATION: (26)..(26)

```
<223> OTHER INFORMATION: n can be A or G

<400> SEQUENCE: 15
acctcctccc ataaattgca gaatcnattc ccttcctgcc cactctcagt g         51
```